US011421029B2

(12) United States Patent
Xue et al.

(10) Patent No.: US 11,421,029 B2
(45) Date of Patent: Aug. 23, 2022

(54) RECOMBINANT BISPECIFIC ANTIBODIES TO PD-L1 AND CTLA-4

(71) Applicant: SICHUAN KELUN-BIOTECH BIOPHARMACEUTICAL CO., LTD., Sichuan (CN)

(72) Inventors: Tongtong Xue, Sichuan (CN); Liang Xiao, Sichuan (CN); Dengnian Liu, Sichuan (CN); Hu Long, Sichuan (CN); Jiangjiang Hu, Sichuan (CN); Yamin Cui, Sichuan (CN); Xiaoxi Yuan, Sichuan (CN); Lichun Wang, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 143 days.

(21) Appl. No.: 16/624,408

(22) PCT Filed: Aug. 17, 2018

(86) PCT No.: PCT/CN2018/100971
§ 371 (c)(1),
(2) Date: Dec. 19, 2019

(87) PCT Pub. No.: WO2019/042153
PCT Pub. Date: Mar. 7, 2019

(65) Prior Publication Data
US 2020/0216538 A1 Jul. 9, 2020

(30) Foreign Application Priority Data
Sep. 1, 2017 (CN) .......................... 201710781402.3

(51) Int. Cl.
*C07K 16/28* (2006.01)
*A61K 35/00* (2006.01)
*A61K 39/00* (2006.01)
*A61P 35/00* (2006.01)

(52) U.S. Cl.
CPC .......... *C07K 16/2818* (2013.01); *A61P 35/00* (2018.01); *C07K 16/2827* (2013.01); *A61K 2039/505* (2013.01); *C07K 2317/31* (2013.01); *C07K 2317/565* (2013.01); *C07K 2317/622* (2013.01); *C07K 2317/732* (2013.01); *C07K 2317/734* (2013.01); *C07K 2317/94* (2013.01)

(58) Field of Classification Search
CPC combination set(s) only.
See application file for complete search history.

(56) References Cited

U.S. PATENT DOCUMENTS

2018/0127501 A1* 5/2018 Bernett .............. C07K 16/2803

FOREIGN PATENT DOCUMENTS

| CN | 104974253 A | 10/2015 | |
|----|----|----|----|
| CN | 104987421 A | 10/2015 | |
| CN | 106967172 A | 7/2017 | |
| CN | 107082812 A | 8/2017 | |
| WO | WO-2014/209804 A1 | 12/2014 | |
| WO | WO-2014209804 A1 * | 12/2014 | ......... C07K 16/2803 |
| WO | WO-2015/048312 A1 | 4/2015 | |
| WO | WO-2017/106061 A1 | 6/2017 | |
| WO | WO 2017/215590 * | 6/2017 | ............ C07K 16/28 |
| WO | WO-2017/136562 A2 | 8/2017 | |
| WO | WO-2017/136562 A3 | 8/2017 | |
| WO | WO-2017/136820 A2 | 8/2017 | |

OTHER PUBLICATIONS

International Search Report with English translation and Written Opinion issued in corresponding application No. PCT/CN2018/100971 dated Nov. 14, 2018.
Li et al., "Application of Bispecific Antibody Drugs" Current Biotechnology, vol. 5, No. 6, 2015, ISSN 2095-2341, pp. 420-424.
Brinkmann et al., "The making of bispecific antibodies," MABS, 2017, vol. 9, No. 2, pp. 182-212.
Su et al., "Immune Checkpoint Inhibitors: Therapeutic Tools for Breast Cancer," Asian Pacific Journal of Cancer Prevention, 2016, vol. 17, pp. 905-910.
Extended European Search Report dated Feb. 15, 2021 in corresponding European Application No. 18851360.0 (11 pgs.).
Notice of Reasons for Refusal dated Jun. 6, 2022 issued in JP Application No. 2019-572582, with English translation, 7 pages.

* cited by examiner

*Primary Examiner* — Laura B Goddard
*Assistant Examiner* — Sarah A Alsomairy
(74) *Attorney, Agent, or Firm* — Foley & Lardner LLP

(57) ABSTRACT

Provided are a recombinant bispecific antibody against CTLA-4 and PDL-1, a nucleic acid molecule for encoding the antibody, a vector and a host cell comprising the nucleic acid molecule, and a method for preparing the antibody. Also provided are a pharmaceutical composition comprising the bispecific antibody, and usage of the bispecific antibody in preparation of the pharmaceutical composition.

40 Claims, 8 Drawing Sheets
Specification includes a Sequence Listing.

AB03        AB04

SEQUENCE LISTING

<160> NUMBER OF SEQ ID NOS: 34

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB01 HCDR1

<400> SEQUENCE: 1

Gly Phe Ser Leu Ser Asn Tyr Asp
1               5

<210> SEQ ID NO 2

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB01 HCDR2

<400> SEQUENCE: 2

Ile Trp Thr Gly Gly Ala Thr
1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB01 HCDR3

<400> SEQUENCE: 3

Val Arg Asp Ser Asn Tyr Arg Tyr Asp Glu Pro Phe Thr Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB01 LCDR1

<400> SEQUENCE: 4

Gln Ser Ile Gly Thr Asn
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB01 LCDR2

<400> SEQUENCE: 5

Tyr Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB01 LCDR3

<400> SEQUENCE: 6

Gln Gln Ser Asn Ser Trp Pro Tyr Thr
1               5
```

```
<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB01 VH

<400> SEQUENCE: 7

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Asn Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Ala Thr Asn Tyr Asn Pro Ala Leu Lys
    50                  55                  60

Ser Arg Leu Thr Ile Ser Arg Asp Asn Ser Lys Asn Gln Val Ser Leu
65                  70                  75                  80

Lys Met Ser Ser Val Thr Ala Ala Asp Thr Ala Val Tyr Tyr Cys Val
                85                  90                  95

Arg Asp Ser Asn Tyr Arg Tyr Asp Glu Pro Phe Thr Tyr Trp Gly Gln
            100                 105                 110

Gly Thr Leu Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB01 mutant VH

<400> SEQUENCE: 8

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Asn Tyr
            20                  25                  30

Asp Ile Ser Trp Ile Arg Gln Pro Pro Gly Lys Cys Leu Glu Trp Leu
        35                  40                  45

Gly Val Ile Trp Thr Gly Gly Ala Thr Asn Tyr Asn Pro Ala Leu Lys
    50                  55                  60

Ser Arg Leu Thr Ile Ser Arg Asp Asn Ser Lys Asn Gln Val Ser Leu
65                  70                  75                  80

Lys Met Ser Ser Val Thr Ala Ala Asp Thr Ala Val Tyr Tyr Cys Val
                85                  90                  95

Arg Asp Ser Asn Tyr Arg Tyr Asp Glu Pro Phe Thr Tyr Trp Gly Gln
            100                 105                 110

Gly Thr Leu Val Thr Val Ser Ser
        115                 120

<210> SEQ ID NO 9
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: AB01 VL

<400> SEQUENCE: 9

Glu Ile Val Leu Thr Gln Ser Pro Asp Thr Leu Ser Val Thr Pro Lys
1               5                   10                  15

Glu Lys Val Thr Leu Thr Cys Arg Ala Ser Gln Ser Ile Gly Thr Asn
            20                  25                  30

Ile His Trp Phe Gln Gln Lys Pro Gly Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Cys Thr Lys Leu Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB01 mutant VL

<400> SEQUENCE: 10

Glu Ile Val Leu Thr Gln Ser Pro Asp Thr Leu Ser Val Thr Pro Lys
1               5                   10                  15

Glu Lys Val Thr Leu Thr Cys Arg Ala Ser Gln Ser Ile Gly Thr Asn
            20                  25                  30

Ile His Trp Phe Gln Gln Lys Pro Gly Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Tyr
                85                  90                  95

Thr Phe Gly Cys Gly Thr Lys Leu Glu Ile Lys
            100                 105

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB01 light chain

<400> SEQUENCE: 11

Glu Ile Val Leu Thr Gln Ser Pro Asp Thr Leu Ser Val Thr Pro Lys
1               5                   10                  15

Glu Lys Val Thr Leu Thr Cys Arg Ala Ser Gln Ser Ile Gly Thr Asn

```
                    20                  25                  30
Ile His Trp Phe Gln Gln Lys Pro Gly Gln Ser Pro Lys Leu Leu Ile
                35                  40                  45

Lys Tyr Ala Ser Glu Ser Ile Ser Gly Val Pro Ser Arg Phe Ser Gly
        50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 12
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB01 heavy chain

<400> SEQUENCE: 12

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Asn Tyr
                20                  25                  30

Asp Ile Ser Trp Ile Arg Gln Pro Pro Gly Lys Gly Leu Glu Trp Leu
            35                  40                  45

Gly Val Ile Trp Thr Gly Gly Ala Thr Asn Tyr Asn Pro Ala Leu Lys
        50                  55                  60

Ser Arg Leu Thr Ile Ser Arg Asp Asn Ser Lys Asn Gln Val Ser Leu
65                  70                  75                  80

Lys Met Ser Ser Val Thr Ala Ala Asp Thr Ala Val Tyr Tyr Cys Val
                85                  90                  95

Arg Asp Ser Asn Tyr Arg Tyr Asp Glu Pro Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145                 150                 155                 160
        Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                        195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Ala Ala Gly Ala
        225                 230                 235                 240

Pro Ser Val Phe Leu Phe Pro Pro Lys Pro Lys Asp Thr Leu Met Ile
                        245                 250                 255

Ser Arg Thr Pro Glu Val Thr Cys Val Val Val Asp Val Ser His Glu
                        260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly Lys
            450

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB02 HCDR1

<400> SEQUENCE: 13

Gly Phe Thr Phe Ser Ser Tyr Thr
1               5

<210> SEQ ID NO 14
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB02 HCDR2

<400> SEQUENCE: 14

Ile Ser Tyr Asp Gly Asn Asn Lys
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB02 HCDR3

<400> SEQUENCE: 15

Ala Arg Thr Gly Trp Leu Gly Pro Phe Asp Tyr
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB02 LCDR1

<400> SEQUENCE: 16

Gln Ser Val Gly Ser Ser Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB02 LCDR2

<400> SEQUENCE: 17

Gly Ala Phe
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: AB02 LCDR3

<400> SEQUENCE: 18

Gln Gln Tyr Gly Ser Ser Pro Trp Thr
1               5

<210> SEQ ID NO 19
<211> LENGTH: 118

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB02 VH

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 20
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB02 mutant VH

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Cys Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: AB02 VL

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB02 mutant VL

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Cys Gly Thr Lys Val Glu Ile Lys
            100                 105

<210> SEQ ID NO 23
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB02 light chain

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

```
Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 24
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB02 heavy chain

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
 50                     55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: S2

<400> SEQUENCE: 25

Gly Gly Gly Gly Ser Gly Gly Gly Ser Gly Gly Gly Gly Ser Gly
1               5                   10                  15

Gly Gly Gly Ser
            20

<210> SEQ ID NO 26
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: S1

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: S1

<400> SEQUENCE: 27

Gly Gly Gly Gly Ser Gly Gly Gly Gly Ser
1               5                   10

<210> SEQ ID NO 28
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB03 first polypeptide chain amino acid
      sequence

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Cys Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Val Val Gln Pro Gly Arg
    130                 135                 140

Ser Leu Arg Leu Ser Cys Ala Ala Ser Gly Phe Thr Phe Ser Ser Tyr
145                 150                 155                 160

Thr Met His Trp Val Arg Gln Ala Pro Gly Lys Cys Leu Glu Trp Val
                165                 170                 175

Thr Phe Ile Ser Tyr Asp Gly Asn Asn Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205
```

-continued

Leu Gln Met Asn Ser Leu Arg Ala Glu Asp Thr Ala Ile Tyr Tyr Cys
210                 215                 220

Ala Arg Thr Gly Trp Leu Gly Pro Phe Asp Tyr Trp Gly Gln Gly Thr
225                 230                 235                 240

Leu Val Thr Val Ser Ser Gly Gly Gly Ser Gly Gly Gly Gly Ser
            245                 250                 255

Gly Gly Gly Gly Ser Gln Val Gln Leu Gln Glu Ser Gly Pro Gly Leu
            260                 265                 270

Val Lys Pro Ser Glu Thr Leu Ser Ile Thr Cys Thr Val Ser Gly Phe
            275                 280                 285

Ser Leu Ser Asn Tyr Asp Ile Ser Trp Ile Arg Gln Pro Pro Gly Lys
290                 295                 300

Gly Leu Glu Trp Leu Gly Val Ile Trp Thr Gly Gly Ala Thr Asn Tyr
305                 310                 315                 320

Asn Pro Ala Leu Lys Ser Arg Leu Thr Ile Ser Arg Asp Asn Ser Lys
            325                 330                 335

Asn Gln Val Ser Leu Lys Met Ser Ser Val Thr Ala Ala Asp Thr Ala
            340                 345                 350

Val Tyr Tyr Cys Val Arg Asp Ser Asn Tyr Arg Tyr Asp Glu Pro Phe
            355                 360                 365

Thr Tyr Trp Gly Gln Gly Thr Leu Val Thr Val Ser Ser Ala Ser Thr
            370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
            405                 410                 415

Pro Val Thr Val Ser Trp Asn Ser Gly Ala Leu Thr Ser Gly Val His
            420                 425                 430

Thr Phe Pro Ala Val Leu Gln Ser Ser Gly Leu Tyr Ser Leu Ser Ser
            435                 440                 445

Val Val Thr Val Pro Ser Ser Ser Leu Gly Thr Gln Thr Tyr Ile Cys
            450                 455                 460

Asn Val Asn His Lys Pro Ser Asn Thr Lys Val Asp Lys Lys Val Glu
465                 470                 475                 480

Pro Lys Ser Cys Asp Lys Thr His Thr Cys Pro Pro Cys Pro Ala Pro
            485                 490                 495

Glu Leu Leu Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
            515                 520                 525

Asp Val Ser His Glu Asp Pro Glu Val Lys Phe Asn Trp Tyr Val Asp
530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
            565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
            595                 600                 605

Glu Pro Gln Val Tyr Thr Leu Pro Pro Ser Arg Asp Glu Leu Thr Lys
610                 615                 620

Asn Gln Val Ser Leu Thr Cys Leu Val Lys Gly Phe Tyr Pro Ser Asp

```
                625                 630                 635                 640
Ile Ala Val Glu Trp Glu Ser Asn Gly Gln Pro Glu Asn Asn Tyr Lys
                    645                 650                 655

Thr Thr Pro Pro Val Leu Asp Ser Asp Gly Ser Phe Phe Leu Tyr Ser
                    660                 665                 670

Lys Leu Thr Val Asp Lys Ser Arg Trp Gln Gln Gly Asn Val Phe Ser
                    675                 680                 685

Cys Ser Val Met His Glu Ala Leu His Asn His Tyr Thr Gln Lys Ser
                    690                 695                 700

Leu Ser Leu Ser Pro Gly Lys
705                 710

<210> SEQ ID NO 29
<211> LENGTH: 706
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB04 first polypeptide chain amino acid
      sequence

<400> SEQUENCE: 29

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Asn Tyr
                20                  25                  30

Asp Ile Ser Trp Ile Arg Gln Pro Pro Gly Lys Gly Leu Glu Trp Leu
            35                  40                  45

Gly Val Ile Trp Thr Gly Gly Ala Thr Asn Tyr Asn Pro Ala Leu Lys
        50                  55                  60

Ser Arg Leu Thr Ile Ser Arg Asp Asn Ser Lys Asn Gln Val Ser Leu
65                  70                  75                  80

Lys Met Ser Ser Val Thr Ala Ala Asp Thr Ala Val Tyr Tyr Cys Val
                85                  90                  95

Arg Asp Ser Asn Tyr Arg Tyr Asp Glu Pro Phe Thr Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Ser Glu Ile Val Leu
450                 455                 460

Thr Gln Ser Pro Gly Thr Leu Ser Leu Ser Pro Gly Glu Arg Ala Thr
465                 470                 475                 480

Leu Ser Cys Arg Ala Ser Gln Ser Val Gly Ser Ser Tyr Leu Ala Trp
                485                 490                 495

Tyr Gln Gln Lys Pro Gly Gln Ala Pro Arg Leu Leu Ile Tyr Gly Ala
            500                 505                 510

Phe Ser Arg Ala Thr Gly Ile Pro Asp Arg Phe Ser Gly Ser Gly Ser
        515                 520                 525

Gly Thr Asp Phe Thr Leu Thr Ile Ser Arg Leu Glu Pro Glu Asp Phe
530                 535                 540

Ala Val Tyr Tyr Cys Gln Gln Tyr Gly Ser Ser Pro Trp Thr Phe Gly
545                 550                 555                 560

Cys Gly Thr Lys Val Glu Ile Lys Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Val Glu Ser Gly Gly Gly Val Val Gln Pro Gly Arg Ser Leu Arg Leu
        595                 600                 605

Ser Cys Ala Ala Ser Gly Phe Thr Phe Ser Ser Tyr Thr Met His Trp
610                 615                 620

Val Arg Gln Ala Pro Gly Lys Cys Leu Glu Trp Val Thr Phe Ile Ser
625                 630                 635                 640

Tyr Asp Gly Asn Asn Lys Tyr Tyr Ala Asp Ser Val Lys Gly Arg Phe
                645                 650                 655

Thr Ile Ser Arg Asp Asn Ser Lys Asn Thr Leu Tyr Leu Gln Met Asn
            660                 665                 670

Ser Leu Arg Ala Glu Asp Thr Ala Ile Tyr Tyr Cys Ala Arg Thr Gly
```

```
            675                 680                 685
Trp Leu Gly Pro Phe Asp Tyr Trp Gly Gln Gly Thr Leu Val Thr Val
    690                 695                 700

Ser Ser
705

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: IgG-Kappa signal peptide amino acid

<400> SEQUENCE: 30

Met Arg Ala Trp Ile Phe Phe Leu Leu Cys Leu Ala Gly Arg Ala Leu
1               5                   10                  15

Ala

<210> SEQ ID NO 31
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB01-scFv

<400> SEQUENCE: 31

Glu Ile Val Leu Thr Gln Ser Pro Asp Thr Leu Ser Val Thr Pro Lys
1               5                   10                  15

Glu Lys Val Thr Leu Thr Cys Arg Ala Ser Gln Ser Ile Gly Thr Asn
            20                  25                  30

Ile His Trp Phe Gln Gln Lys Pro Gly Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Tyr
                85                  90                  95

Thr Phe Gly Cys Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Ile Thr Cys Thr Val Ser Gly Phe Ser Leu Ser Asn Tyr Asp
145                 150                 155                 160

Ile Ser Trp Ile Arg Gln Pro Pro Gly Lys Cys Leu Glu Trp Leu Gly
                165                 170                 175

Val Ile Trp Thr Gly Gly Ala Thr Asn Tyr Asn Pro Ala Leu Lys Ser
            180                 185                 190

Arg Leu Thr Ile Ser Arg Asp Asn Ser Lys Asn Gln Val Ser Leu Lys
        195                 200                 205

Met Ser Ser Val Thr Ala Ala Asp Thr Ala Val Tyr Tyr Cys Val Arg
```

```
                210                 215                 220
Asp Ser Asn Tyr Arg Tyr Asp Glu Pro Phe Thr Tyr Trp Gly Gln Gly
225                 230                 235                 240

Thr Leu Val Thr Val Ser Ser
                245

<210> SEQ ID NO 32
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AB02-scFv

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Cys Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Val Val Gln Pro Gly Arg
    130                 135                 140

Ser Leu Arg Leu Ser Cys Ala Ala Ser Gly Phe Thr Phe Ser Ser Tyr
145                 150                 155                 160

Thr Met His Trp Val Arg Gln Ala Pro Gly Lys Cys Leu Glu Trp Val
                165                 170                 175

Thr Phe Ile Ser Tyr Asp Gly Asn Asn Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Ile Tyr Tyr Cys
    210                 215                 220

Ala Arg Thr Gly Trp Leu Gly Pro Phe Asp Tyr Trp Gly Gln Gly Thr
225                 230                 235                 240

Leu Val Thr Val Ser Ser
                245

<210> SEQ ID NO 33
<211> LENGTH: 330
<212> TYPE: PRT
<213> ORGANISM: Homo sapiens
<220> FEATURE:
<223> OTHER INFORMATION: Constant region of immunoglobulin heavy chain

<400> SEQUENCE: 33
```

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 107
<212> TYPE: PRT
<213> ORGANISM: Homo sapiens
<220> FEATURE:
<223> OTHER INFORMATION: Constant region of immunoglobulin light chain

<400> SEQUENCE: 34

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30
```

-continued

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

RECOMBINANT BISPECIFIC ANTIBODIES TO PD-L1 AND CTLA-4

CROSS-REFERENCE TO RELATED APPLICATIONS

This application is a U.S. National Stage Application under 35 U.S.C. § 371 of PCT International Application No. PCT/CN2018/100971, filed on Aug. 17, 2018, which claims the benefit of priority to China Application No. CN 201710781402.3 filed on Sep. 1, 2017, the disclosures of each of the aforementioned patent applications are hereby incorporated by reference in their entireties for all purposes.

The instant application contains a Sequence Listing which has been submitted electronically in ASCII format and is hereby incorporated by reference in its entirety. Said ASCII copy, created on Mar. 21, 2022, is named 202203-038873-0114_SL.txt and is 46,710 bytes in size.

TECHNICAL FIELD

The present invention relates to the field of biomedicine, in particular to the field of prevention and/or treatment of diseases associated with CTLA-4 and/or PDL-1. In particular, the invention relates to bispecific antibodies that specifically bind to CTLA-4 and PDL-1, or PDL-1 and CTLA-4.

BACKGROUND ART

The PD-1/PDL-1 signaling pathway plays an important role in regulating immune tolerance, microbial infection, and tumor immune evasion. PD-1 (programmed cell death 1) is expressed mainly on immune cells such as T cells, and PDL-1, the PD-1 ligand, is mainly shown high expression in many human tumor tissues. The expression of PDL-1 protein is detected in many human tumor tissues, such as breast cancer, lung cancer, gastric cancer, intestinal cancer, esophageal cancer, ovarian cancer, cervical cancer, kidney cancer, bladder cancer, pancreatic cancer, glioma and melanoma by immunohistochemical methods, and the expression level of PDL-1 is closely related to the clinical manifestation and prognosis of patients.

Blocking the PD-1/PDL-1 signaling pathway activates suppressed T cells to attack cancer cells. Blocking PD-1/PDL-1 signaling can promote proliferation of tumor antigen specific T cells, which could play a role in killing tumor cells, thereby inhibiting local tumor growth (Julie R et al., 2012, N Engl J Med. 366: 2455-2465); PDL-1 mAb up-regulates the secretion of IFN-γ in infiltrating CD8+ T cells, suggesting that the blockade of PD-1/PDL-1 signaling plays a role in tumor immune responses for the purpose of inducing immune responses (Blank C et al., 2006, Int. J. Cancer. 119:317-327).

In addition, PDL-1 can also bind to B7-1 in vivo. Studies have shown that the PDL-1/B7-1 complex is also a negative signal for T cell activation, and the binding of these two molecules can lead to decreased expression of T cells surface activation markers, and inhibition of T cells proliferation, and so on.

Cytotoxic T lymphocyte associated antigen-4 (also referred to as CTLA-4) and CD28 molecules are closely related in term of gene structure, chromosomal location, sequence homology and gene expression, they are both receptors for the co-stimulatory molecule B7 and are mainly expressed on the surface of activated T cells. CTLA-4 could inhibit the activation of mouse and human T cells upon binding to B7, and play a negative regulatory role in T cells activation.

Currently, drug regulatory authorities have approved Ipilimumab (Yervoy®) targeting CTLA-4, and Nivolumab (Opdivo®), Pembrolizumab (Keytruda®), Atezolizumab (Tecentriq®), Durvalumab (Imfinzir®), etc. targeting PD-1 and PDL-1.

Ipilimumab (Yervoy®) is approved by the FDA for the treatment of advanced melanoma, but the injection of this antibody has serious and even fatal immune-mediated adverse effects. These immune-mediated adverse effects may involve any organ system; however, the most common serious immune-mediated adverse effects are enterocolitis, hepatitis, dermatitis (including toxic epidermal necrolysis), neuropathy, and endocrine diseases. Most of these immune-mediated responses initially appear in the course of treatment; another small fraction occurs within a few weeks after drug discontinuation. For severe immune-mediated responses, Yervoy® should be permanently discontinued, and systemic high-dose glucocorticoid therapy should be initiated immediately.

Bispecific antibody (BsAb) is a class of dual-affinity combinatorial antibody, which is usually bivalent (also could be tetravalent and hexavalent), i.e. having two antigen-binding arms, and thus having the functions of specific binding to two different antigens. Chinese patent application CN106967172A discloses anti-CTLA-4-anti-PD-1 bifunctional antibodies, pharmaceutical compositions and uses thereof. CN104987421A also discloses dual variable domain immunoglobulins which specifically bind to PD-1 and/or CTLA-4. Meanwhile, in August 2017, Bristol-Myers Squibb published the top-level data of phase III clinical study CM214, which compared Opdivo/Yervoy combination as the first-line therapy with Sutent (sunitinib) in advanced kidney cancer (RCC) patients. The response rate of Opdivo/Yervoy combination was 41.6% and that of the Sutent was 26.5%, reaching this primary endpoint. However, this combination missed another primary endpoint of mPFS (median progression-free survival) (11.6 vs 8.4 months, but did not reach statistical significance). In July 2017, AstraZeneca announced the mid-term analysis result of the combination of its PDL-1 antibody Durvalumab (trade name Imfinzi) and the CTLA-4 antibody Tremelimumab in a phase III clinical trial called Mystic. This trial compared the effects of Durva/Treme combination and standard chemotherapy on PFS (progression-free survival) and OS (overall survival) in first-line NSCLC patients with PDL-1>25%, the results showed this combination did not improve PFS (one of the primary endpoints in the trial). Available data shown that there is very small chance that Durvalumab alone would improve PFS.

Therefore, there is still an unmet need for diseases such as autoimmune diseases or tumors, and it is urgent and necessary to develop innovative treatment methods and drugs that are more effective and have fewer side effects.

Content of the Invention

In the present application, by in-depth research, the inventors have developed a bispecific antibody specifically binding to CTLA-4 and PDL-1, or PDL-1 and CTLA-4, a nucleic acid molecule encoding the bispecific antibody, a vector comprising the nucleic acid molecule, a method for preparing the bispecific antibody, a pharmaceutical composition comprising the bispecific antibody, uses of the pharmaceutical composition in preparation of a medicament, uses or methods of the bispecific antibody in diagnosing/treating/preventing diseases associated with CTLA-4 and PDL-1 (such as autoimmune diseases or tumors), and a kit comprising the bispecific antibody.

Bispecific Antibodies

Thus, in one aspect, the invention provides a bispecific antibody comprising proteins or polypeptides that bind to both the antigen PDL-1 and the antigen CTLA-4.

In certain preferred embodiments, the bispecific antibody comprises:

1) a first antibody that specifically binds to the first antigen, the first antibody comprising heavy chains (HCs) and light chains (LCs); and, 2) an antibody fragment that specifically binds to the second antigen comprising a heavy chain variable region (VH) and a light chain variable region (VL) (e.g., Fv, scFv, di-scFv):

wherein the antibody fragment is linked to the N-terminus or C-terminus of the heavy chain or light chain of the first antibody;

the first antigen is CTLA-4 and the second antigen is PDL-1; or, the first antigen is PDL-1 and the second antigen is CTLA-4.

In certain preferred embodiments, the antibody fragment is an scFv.

In certain preferred embodiments, the bispecific antibody comprises one said first antibody and two said scFvs; and, the first antibody comprises two HCs and two LCs, wherein the heavy chain variable region (VH) of one of HCs of said first antibody and the light chain variable region (VL) of one of LCs of said first antibody form an antigen binding site, the VH of the other HC and VL of the other LC form an antigen binding site.

In certain preferred embodiments, each of the scFvs is linked to the N-terminus or C-terminus of the two heavy chains or two light chains of the first antibody, respectively.

In certain preferred embodiments, each of the scFvs is linked to the N-terminus of the two heavy chains of the first antibody, respectively. In certain preferred embodiments, each of the scFvs is linked to the C-terminus of the two heavy chains of the first antibody, respectively. In certain preferred embodiments, the first antigen is PDL-1, the second antigen is CTLA-4, and the scFvs that bind to the second antigen are linked to the C-terminus of the two heavy chains of the first antibody.

In certain preferred embodiments, each of the scFvs is linked to the N-terminus of the two light chains of the first antibody, respectively. In certain preferred embodiments, each of the scFvs is linked to the C-terminus of the two light chains of the first antibody, respectively.

In certain preferred embodiments, one of the scFvs is linked to the N-terminus of the heavy chain or light chain of the first antibody, and the other scFv is linked to the C-terminus of heavy chain or light chain of the first antibody.

In certain preferred embodiments, the bispecific antibody of the invention comprises:

1) a first antibody that specifically binds to the first antigen, the first antibody comprising heavy chains (HCs) and light chains (LCs); and 2) an scFv that specifically binds to the second antigen; the bispecific antibody comprises one said first antibody and two said scFvs; and the first antibody comprises two HCs and two LCs, wherein the VH region of one of the HCs and the VL region of one of the LCs form an antigen binding site, the VH region of the other HC and the VL region of the other LC form an antigen binding site; each of said scFvs is linked to the N-terminus of two heavy chains of said first antibody respectively; or, each of said scFvs is linked to the C-terminus of two heavy chains of said first antibody respectively; the first antigen is PDL-1 and the second antigen is CTLA-4. In certain preferred embodiments, each scFv is linked to the N-terminus or C-terminus of each heavy chain of the first antibody via a linker S1. In certain preferred embodiments, the VH and VL of scFv are linked via a linker S2. In certain preferred embodiments, the structure of the scFv is NH2-VL-S2-VH—COOH, wherein the S2 is a linker.

In certain preferred embodiments, the heavy chain of the first antibody comprises a heavy chain variable region (VH) and a CH1 domain, and the light chain comprises a light chain variable region (VL) and a light chain constant region (CL). In such embodiments, the first antibody can be a Fab fragment, a Fab' fragment or a F(ab')$_2$ fragment. In certain preferred embodiments, the heavy chain of the first antibody comprises a heavy chain variable region (VH) and a heavy chain constant region (CH), and the light chain comprises a light chain variable region (VL) and light chain constant region (CL). In such embodiments, the first antibody can be a full length antibody.

In certain preferred embodiments, the heavy chain of the first antibody is an IgG isotype, such as IgG1, IgG2, IgG3 or IgG4; preferably a human IgG isotype. In certain embodiments, the heavy chain of the first antibody is a human IgG1 isotype. In certain preferred embodiments, the light chain of the first antibody is a Kappa isotype, preferably a human Kappa isotype.

In certain preferred embodiments, the two HCs of the first antibody comprise the same CDRs and/or the two LCs of the first antibody comprise the same CDRs.

In certain preferred embodiments, the two HCs of the first antibody comprise the same VHs; and/or the two LCs of the first antibody comprise the same VLs.

In certain preferred embodiments, the two HCs of the first antibody have the same amino acid sequence; and/or the two LCs of the first antibody have the same amino acid sequence.

In certain preferred embodiments, the two scFvs have the same or different amino acid sequences. In certain preferred embodiments, the two scFvs have the same amino acid sequence.

In certain preferred embodiments, the bispecific antibody comprises two first polypeptide chains and two second polypeptide chains, wherein for each of the polypeptide chains:

a) each of the first polypeptide chains independently comprises a heavy chain (HC) of the first antibody and a said scFv; and b) each of the second polypeptide chains independently comprises a light chain (LC) of the first antibody;

wherein the scFv is linked to the N-terminus or C-terminus of the HC of the first antibody via a linker S1.

In certain preferred embodiments, the bispecific antibody comprises two first polypeptide chains and two second polypeptide chains, wherein for each of the polypeptide chains:

i) each of the first polypeptide chains independently comprises a light chain (LC) of the first antibody and a said scFv; and ii) each of the second polypeptide chains independently comprises a heavy chain (HC) of the first antibody, wherein the scFv is linked to the N-terminus or C-terminus of the LC of the first antibody via a linker S1.

In certain preferred embodiments, the N-terminus or C-terminus of the scFv is linked to the C-terminus or N-terminus of the linker S1.

In certain preferred embodiments, the scFv has the structure: $NH_2$-VH-S2-VL-COOH or $NH_2$-VL-S2-VH-COOH, wherein the S2 is a linker.

In certain preferred embodiments, the linker S1 and/or linker S2 is a peptide linker, for example having an amino acid sequence set forth in $(G_mS_n)_x$, wherein each of m, n are independently selected from integers from 1 to 8 (e.g. 1, 2, 3, 4, 5, 6, 7, or 8), x is independently selected from integers from 1 to 20 (e.g., 1, 2, 3, 4, 5, 6, 7, 8, 9, 10, 11, 12, 13, 14, 15, 16, 17, 18, 19 or 20). In certain preferred embodiments, the linker S1 and/or S2 has an amino acid sequence set forth in $(G_4S)x$, and x is independently selected from integers from 1 to 6.

In certain preferred embodiments, the linker S1 and/or linker S2 has an amino acid sequence selected from the group consisting of: SEQ ID NO: 25, SEQ ID NO: 26, and SEQ ID NO: 27.

In certain preferred embodiments, the linker S2 has an amino acid sequence set forth in $(G_4S)_4$, i.e. GGGGSGGGGSGGGGSGGGGS (SEQ ID NO: 25). In certain preferred embodiments, when the scFv is linked to the N-terminus of the heavy or light chain of the first antibody, the linker S1 has an amino acid sequence set forth in $(G_4S)_3$, i.e. GGGGSGGGGSGGGGS (SEQ ID NO: 26); when the scFv is linked to the C-terminus of the heavy or light chain of the first antibody, the linker S1 has an amino acid sequence set forth in $(G_4S)_2$, namely GGGGSGGGGS (SEQ ID NO: 27).

In certain preferred embodiments, a disulfide bond exists between the VH and VL of the scFv. Methods for introducing a disulfide bond between the VH and VL of an antibody are well known in the art, for example, see U.S. Pat. No. 5,747,654; Rajagopal et al., Prot. Engin. 10(1997)1453-1459, Reiter et al., Nature Biotechnology 14(1996)1239-1245; Reiter et al., Protein Engineering 8(1995)1323-1331; Webber et al., Molecular Immunology 32(1995)249-258; Reiter et al., Immunity 2(1995)281-287; Reiter et al., JBC 269(1994)18327-18331; Reiter et al., Inter. J. of Cancer 58(1994)142-149; or Reiter et al., Cancer Res. 54(1994) 2714-2718, which are incorporated herein by reference.

In certain preferred embodiments, the amino acid at the position 44 of the VH and the amino acid at the position 100 of the VL of the scFv are respectively cysteines, wherein the amino acid position referred to is according to Kabat numbering system. The VH and VL of the scFv are linked by a disulfide bond formed between two cysteine residues at the position 44 of VH and the position 100 of VL, respectively.

In certain preferred embodiments, the first antibody specifically binds to CTLA-4 and the scFv specifically bind to PDL-1, wherein the scFv comprises:
HCDR1 set forth in SEQ ID NO: 1; HCDR2 set forth in SEQ ID NO: 2; and HCDR3 set forth in SEQ ID NO: 3; LCDR1 set forth in SEQ ID NO: 4; LCDR2 set forth in SEQ ID NO: 5; and LCDR3 set forth in SEQ ID NO: 6.

In certain preferred embodiments, the first antibody specifically binds to CTLA-4 and the scFv specifically binds to PDL-1, wherein:
the first antibody comprises:
HCDR1 set forth in SEQ ID NO: 13; HCDR2 set forth in SEQ ID NO: 14; and HCDR3 set forth in SEQ ID NO: 15; LCDR1 set forth in SEQ ID NO: 16; LCDR2 set forth in SEQ ID NO: 17; and LCDR3 set forth in SEQ ID NO: 18; and/or.

the scFv comprises;
HCDR1 set forth in SEQ ID NO: 1; HCDR2 set forth in SEQ ID NO: 2; and HCDR3 set forth in SEQ ID NO: 3; LCDR1 set forth in SEQ ID NO: 4; LCDR2 set forth in SEQ ID NO: 5; and LCDR3 set forth in SEQ ID NO: 6.

In certain preferred embodiments, the first antibody comprises: HCDR1 set forth in SEQ ID NO: 13; HCDR2 set forth in SEQ ID NO: 14; and HCDR3 set forth in SEQ ID NO: 15; LCDR1 set forth in SEQ ID NO: 16; LCDR2 set forth in SEQ ID NO: 17; and LCDR3 set forth in SEQ ID NO: 18; and the scFv comprises: HCDR1 set forth in SEQ ID NO: 1; HCDR2 set forth in SEQ ID NO: 2; and HCDR3 set forth in SEQ ID NO: 3; LCDR1 set forth in SEQ ID NO: 4; LCDR2 set forth in SEQ ID NO: 5; and LCDR3 set forth in SEQ ID NO: 6.

In certain preferred embodiments, the amino acid sequence of the heavy chain variable region (VH) of the first antibody has at least 90%, 91%, 92%, 93%, 94%, 95%, 96%, 97%, 98%, 99%, or 10)0% sequence identity to the amino acid sequence of the heavy chain variable region set forth in SEQ ID NO: 19; and, the amino acid sequence of the light chain variable region (VL) of the first antibody has at least 90%, 91%, 92%, 93%, 94%, 95%, 96%, 97%, 98%, 99/%, or 100% sequence identity to the amino acid sequence of the light chain variable region set forth in SEQ ID NO: 21; also, the amino acid sequence of the heavy chain variable region (VII) of the scFv has at least 90%, 91%, 92%, 93%, 94%, 95%, 96%, 97%, 98%, 99% or 100% sequence identity to the amino acid sequence of the heavy chain variable region set forth in SEQ ID NO: 7 or SEQ ID NO: 8. The amino acid sequence of the light chain variable region (VL) of the scFv has at least 90%, 91%, 92%, 93%, 94%, 95%, 96%, 97%, 98%, 99% or 100% sequence identity to the amino acid sequence of the light chain variable region set forth in SEQ ID NO: 9 or SEQ ID NO: 10.

In some preferred embodiments, the heavy chain variable region of scFv is selected from the heavy chain variable region set forth in SEQ ID NO: 7, and the light chain variable region of the scFv is selected from the light chain variable region set forth in SEQ ID NO: 9.

In some preferred embodiments, the heavy chain variable region of scFv is selected from the heavy chain variable region set forth in SEQ ID NO: 8, and the light chain variable region of the scFv is selected from the light chain variable region set forth in SEQ ID NO: 10.

In some preferred embodiments, the heavy chain variable region of the rust antibody is selected from the heavy chain variable region set forth in SEQ ID NO: 19, and the light chain variable region of the first antibody is selected from the light chain variable region set forth in SEQ ID NO: 21; and, the heavy chain variable region of the scFv is selected from the heavy chain variable region set forth in SEQ ID NO: 7, and the light chain variable region of the scFv is selected from the light chain variable region set forth in SEQ ID NO: 9.

In some preferred embodiments, the heavy chain variable region of the first antibody is selected from the heavy chain variable region set forth in SEQ ID NO: 19, and the light chain variable region of the first antibody is selected from the light chain variable region set forth in SEQ ID NO: 21; and, the heavy chain variable region of the scFv is selected from the heavy chain variable region set forth in SEQ ID NO: 8, and the light chain variable region of the scFv is selected from the light chain variable region set forth in SEQ ID NO: 10.

In some preferred embodiments, the first antibody comprises: VHs set forth in SEQ ID NO: 19 and VLs set forth in SEQ ID NO: 21;

and, the scFv(s) comprises:

(1) a VH set forth in SEQ ID NO: 7 and a VL set forth in SEQ ID NO: 9, or, (2) a VH set forth in SEQ ID NO: 8 and a VL set forth in SEQ ID NO 10.

In some preferred embodiments, the first antibody specifically binds to PDL-1, and the scFv specifically binds to CTLA-4, wherein the first antibody comprises:

(a) HCDR1 set forth in SEQ ID NO: 1; HCDR2 set forth in SEQ ID NO: 2; and HCDR3 set forth in SEQ ID NO: 3; LCDR1 set forth in SEQ ID NO: 4; LCDR2 set forth in SEQ ID NO: 5; and LCDR3 set forth in SEQ ID NO: 6;

and/or, the scFv(s) comprises:

HCDR1 set forth in SEQ ID NO: 13; HCDR2 set forth in SEQ ID NO: 14; and HCDR3 set forth in SEQ ID NO: 15; LCDR1 set forth in SEQ ID NO: 16; LCDR2 set forth in 17; and LCDR3 set forth in SEQ ID NO: 18.

In some preferred embodiments, the first antibody specifically binds PDL-1, and the scFv specifically binds CTLA-4, wherein the first antibody comprises:

HCDR1 set forth in SEQ ID NO: 1; HCDR2 set forth in SEQ ID NO: 2; and HCDR3 set forth in SEQ ID NO: 3; LCDR11 set forth in SEQ ID NO: 4; LCDR2 set forth in SEQ ID NO: 5; and LCDR3 set forth in SEQ ID NO: 6.

In some preferred embodiments, the first antibody comprises; HCDR1 set forth in SEQ ID NO: 1; HCDR2 set forth in SEQ ID NO: 2; and HCDR3 set forth in SEQ ID NO: 3; LCDR1 set forth in SEQ ID NO: 4; LCDR2 set forth in SEQ ID NO: 5; and LCDR3 set forth in SEQ ID NO: 6, and, the scFv(s) comprises: HCDR1 set forth in SEQ ID NO: 13; HCDR2 set forth in SEQ ID NO: 14; and HCDR3 set forth in SEQ ID NO: 15; LCDR1 set forth in SEQ ID NO: 16; LCDR2 set forth in SEQ ID NO: 17; and LCDR3 set forth in SEQ ID NO: 18.

In certain preferred embodiments, the amino acid sequence of the heavy chain variable region (VH) of the first antibody has at least 90% a, 91%, 92%, 93%, 94%, 95%, 96%, 97%, 98%, 99%, or 100% sequence identity to the amino acid sequence of the heavy chain variable region set forth in SEQ ID NO: 7; and, the amino acid sequence of the light chain variable region (VL) of the first antibody has at least 90%, 91%, 92%, 93%, 94%, 95%, 96%, 97%, 98%, 99%, or 100% sequence identity to the amino acid sequence of the light chain variable region set forth in SEQ ID NO: 9; and the amino acid sequence of the heavy chain variable region (VH) of the scFv has at least 90/o, 91%, 92%, 93%, 94%, 95%, 96%, 97%, 98%, 99%, or 100% sequence identity to the amino acid sequence of the heavy chain variable region set forth in SEQ ID NO: 19 or 20; and the amino acid sequence of the light chain variable region (VL) of the scFv has at least 90%, 91%, 92%, 93%, 94%, 95%, 96%, 97%, 98%, 99%, or 100% sequence identity to the amino acid sequence of the light chain variable region set forth in SEQ ID NO: 21 or SEQ ID NO: 22.

In some preferred embodiments, the heavy chain variable region of the first antibody is selected from the heavy chain variable region set forth in SEQ ID NO: 7; and the light chain variable region of the first antibody is selected from the light chain variable region set forth in SEQ ID NO: 9.

In some preferred embodiments, the heavy chain variable region of the first antibody is selected from the heavy chain variable region set forth in SEQ ID NO: 7; and the light chain variable region of the first antibody is selected from the light chain variable region set forth in SEQ ID NO: 9; and the heavy chain variable region of the scFv is selected from the heavy chain variable region set forth in SEQ ID NO:19 and the light chain variable region of the scFv is selected from the light chain variable region set forth in SEQ ID NO: 21.

In some preferred embodiments, the heavy chain variable region of the first antibody is selected from the heavy chain variable region set forth in SEQ ID NO: 7, and the light chain variable region of the first antibody is selected from the light chain variable region set forth in SEQ ID NO: 9, and the heavy chain variable region of the scFv is selected from the heavy chain variable region set forth in SEQ ID NO:20, and the light chain variable region of the scFv is selected from the light chain variable region set forth in SEQ ID NO: 22.

In some preferred embodiments, the first antibody comprises: a VH set forth in SEQ ID NO: 7 and a VL set forth in SEQ ID NO: 9;

and, the scFv(s) comprises:

(1) a VH set forth in SEQ ID NO: 19 and a VL set forth in SEQ ID NO: 21, or, (2) a VH set forth in SEQ ID NO: 20 and a VL set forth in SEQ ID NO: 22.

In some preferred embodiments, the bispecific antibody comprises two identical first polypeptide chains and two identical second polypeptide chains.

In some preferred embodiments, the first polypeptide chain has an amino acid sequence selected from the amino acid sequence set forth in any one of SEQ ID NOs: 28 and 29, and/or, the second polypeptide chain has an amino acid sequence selected from the amino acid sequence set forth in any one of SEQ ID NOs: 11 and 23.

In some preferred embodiments, the bispecific antibody comprises:

(1) the first polypeptide chain set forth in SEQ ID NO: 28 and the second polypeptide chain set forth in SEQ ID NO: 11;

(2) the first polypeptide chain set forth in SEQ ID NO: 29 and the second polypeptide chain set forth in SEQ ID NO: 11;

(3) the first polypeptide chain set forth in SEQ ID NO: 28 and the second polypeptide chain set forth in SEQ ID NO: 23; or (4) the first polypeptide chain set forth in SEQ ID NO: 29 and the second polypeptide chain set forth in SEQ ID NO: 23.

In some embodiments, the first antibody of the bispecific antibody of the invention comprises: a CH as indicated by Uniprot Accession No. P01857; and/or, a CL as indicated by Uniprot Accession No. P01834. Optionally, wherein the CH comprises mutations, in which the amino acids at the positions 117, 118, and 120 of the CH as indicated by UniProt Accession No. P01857 are mutated to A; or, the CH comprises a mutation, in which the amino acid at the position 97 in the CH as indicated by UniProtAccession No. P01857 is mutated to R.

In some embodiments, the bispecific antibody of the present invention has an antibody-dependent cell-mediated cytotoxicity (ADCC) activity. In some embodiments, the bispecific antibody of the present invention has an antibody-dependent cell-mediated cytotoxicity (ADCC) activity, and also has a complement dependent cytotoxicity (CDC) activity. In some preferred embodiments, the bispecific antibody of the present invention has an enhanced antibody-dependent cell-mediated cytotoxicity (ADCC) activity, and/or an enhanced complement-dependent cytotoxicity (CDC) activity. In some preferred embodiments, the enhanced ADCC and/or CDC activity is caused by a mutation in the CH of the first antibody of the bispecific antibody.

In another aspect, the bispecific antibody of the present invention has the binding activity to the first antigen equal to or weaker than that of the parental antibody of said first antibody; and in some preferred embodiments, the bispecific antibody of the present invention has the binding activity to the second antigen equal to or weaker than that of the parental antibody of said scFv. In some preferred embodiments, the bispecific antibody of the present invention has the binding activity to the first antigen equal to or weaker than that of the parental antibody of said first antibody and the binding activity to the second antigen equal to or weaker than that of the parental antibody of said scFv. In some preferred embodiments, the bispecific antibody of the present invention has the binding activity to the first antigen equal to that of the parental antibody of said first antibody and the binding activity to the second antigen weaker than that of the parental antibody of said scFv. In some preferred embodiments, the bispecific antibody of the present invention has the binding activity equal to that of the parental antibody binding to PDL-1 parental antibody. In some preferred embodiments, the bispecific antibody of the present invention has the binding activity weaker than that of the parental antibody binding to CTLA-4 parental antibody. In some preferred embodiments, the bispecific antibody of the present invention has the binding activity equal to that of the parental antibody binding to PDL-1, and has the binding activity weaker than that of the parental antibody binding to CTLA-4.

In another aspect, the bispecific antibody of the present invention has affinity to CTLA-4 and PDL-1. In some preferred embodiments, the bispecific antibodies of the present invention have the same affinity for CTLA-4 and PDL-1 as their respective parental antibodies. In some preferred embodiments, the bispecific antibody of the present invention has the same affinity to PDL-1 as its parental antibody. In some preferred embodiments, the bispecific antibody of the present invention has the same affinity to CTLA-4 as its parental antibody. In some preferred embodiments, the bispecific antibody of the present invention has a weaker affinity for CTLA-4 than its parental antibody. In some preferred embodiments, the bispecific antibody of the present invention has the same affinity to PDL-1 as its parental antibody, and weaker affinity to CTLA-4 than its parental antibody.

In another aspect, the bispecific antibody of the present invention has good thermal stability. In some preferred embodiments, the bispecific antibody of the present invention have substantially the same thermal stability as that of parental antibody.

The Expression of Bispectck Antibody

In another aspect, the present invention provides an isolated nucleic acid molecule, which comprises a nucleotide sequence encoding the bispecific antibody in the present invention. In certain preferred embodiments, the isolated nucleic acid molecule encodes the bispecific antibody of the present invention.

In certain preferred embodiments, the isolated nucleic acid molecule comprises a nucleotide sequence encoding the first polypeptide chain of the present invention. In certain preferred embodiments, the isolated nucleic acid molecule comprises a nucleotide sequence encoding the second polypeptide chain of the present invention. In certain preferred embodiments, the isolated nucleic acid molecule comprises a nucleotide sequence encoding the first polypeptide chain and a nucleotide sequence encoding the second polypeptide chain of the present invention.

In another aspect, the present invention provides a vector (e.g., a cloning vector or an expression vector), which comprises the isolated nucleic acid molecule of the present invention.

In certain preferred embodiments, the vector comprises a nucleotide sequence encoding the first polypeptide chain of the present invention. In certain preferred embodiments, the vector comprises a nucleotide sequence encoding the second polypeptide chain of the present invention. In certain preferred embodiments, the vector comprises a nucleotide sequence encoding the first polypeptide chain and a nucleotide sequence encoding the second polypeptide chain of the present invention.

In certain preferred embodiments, the vector of the present invention is, for example, a plasmid, cosmid, phage, and the like. In certain preferred embodiments, the vector is capable of expressing the bispecific antibody of the present invention, the first polypeptide chain of the present invention or the second polypeptide chain of the present invention in a test subject (e.g., a mammal, e.g., human).

In another aspect, the present invention provides a host cell comprising the isolated nucleic acid molecule of the present invention or the vector of the present invention. Such a host cell include, but are not limited to, a prokaryotic cell such as an *E. coli* cell, and an eukaryotic cell such as a yeast cell, an insect cell, a plant cell, and an animal cell (e.g., a mammalian cell, such as a mouse cell, a human cell, etc.). In certain preferred embodiments, the host cell of the invention is a mammalian cell, such as a CHO (e.g., CHO-K1, CHO-S, CHO DG44) or a HEK293 cell.

In another aspect, the present invention provides a method for preparing the bispecific antibody of the present invention, which comprises, culturing the host cell of the present invention under a condition which permits the bispecific antibody to be expressed, and recovering the bispecific antibody from the cultured host cell culture.

In certain preferred embodiments, the method comprises:

(1) constructing an expression vector that comprises a nucleotide sequence encoding the first polypeptide chain and a nucleotide sequence encoding the second polypeptide chain; or, constructing a first expression vector comprising a nucleotide sequence encoding the first polypeptide chain and a second expression vector comprising a nucleotide sequence encoding the second polypeptide chain;

(2) transforming the expression vector described in step (1) into a host cell; or, transforming the first expression vector and the second expression vector described in step (1) into a host cell;

(3) culturing the host cell described in step (2) under a condition which permits the bispecific antibody of this invention to be expressed; and (4) recovering the bispecific antibody from the cultured host cell culture.

Therapeutic Methods and Pharmaceutical Compositions

The bispecific antibody of the present invention can be used in vitro or in vivo of a test subject to inhibit CTLA-4 activity and PDL-1 activity, to block CTLA-4 and/or PDL-1 signaling pathways, and be used for prevention and/or treatment of diseases associated with CTLA-4 and/or PDL-1 (e.g., autoimmune diseases or tumors or infectious diseases).

Accordingly, in another aspect, the present invention provides a pharmaceutical composition comprising the bispecific antibody of the present invention, and a pharmaceutically acceptable carrier and/or excipient. In certain preferred embodiments, the pharmaceutical composition may also comprise additional pharmaceutically active agents. In certain preferred embodiments, the additional pharmaceutically active agent are drugs used for preventing and/or treating diseases associated with CTLA-4 and/or PDL-1 (e.g., autoimmune diseases or tumors or infectious diseases), such as anti-inflammatory drugs or immunosuppressive agents, such as non-steroidal anti-inflammatory drugs (such as ibuprofen, diclofenac, naproxen, indomethacin, piroxicam, meloxicam, nabumetone, or nimesulide), steroidal anti-inflammatory drugs (such as prednisone, dexamethasone or hydrocortisone), antibodies or antagonists of inflammatory cytokines.

In another aspect, the present invention provides use of the bispecific antibody of the present invention or the pharmaceutical composition of the present invention in the preparation of a medicament for preventing and/or treating diseases associated with CTLA-4 and/or PDL-1 (such as autoimmune diseases or tumors or infectious diseases) in a test subject (e.g., human), and/or for inhibiting the activity of CTLA-4 and/or PDL-1 in vitro or in vivo of a test subject (e.g., human).

In another aspect, the present invention provides a method for preventing and/or treating diseases associated with CTLA-4 and/or PDL-1 (e.g., autoimmune diseases or tumors or infection diseases) in a test subject (e.g. human), and/or for inhibiting the activity of CTLA-4 and/or PDL-1 in vitro or in vitro of a test subject (e.g., human), wherein the method comprises administering to the test subject in need thereof an effective amount of the bispecific antibody of the present invention, or the pharmaceutical composition of the present invention.

In the present invention, the diseases associated with CTLA-4 and/or PDL-1 include, but are not limited to, autoimmune diseases or tumors or infectious diseases, such as a tumor, including but not limited to: adenocarcinoma, leukemia, lymphoma, melanoma, sarcoma or including, but not limited to tumors related to adrenal gland, gallbladder, bone, bone marrow, brain, breast, bile duct, gastrointestinal tract, heart, kidney, liver, lung, muscle, ovary, pancreas, parathyroid gland, penis, prostate, skin, salivary gland, spleen, testicle, thymus, thyroid, and uterus, with an infectious disease including but not limited to hepatitis B, hepatitis A, and HIV.

The bispecific antibody of the present invention or the pharmaceutical composition of the present invention may be formulated into any dosage form known in the medical field, such as tablets, pills, suspensions, emulsions, solutions, gels, capsules, powders, granules, elixirs, lozenges, suppositories, injections (including injection solution, sterile powders for injections and concentrated solutions for injections), inhalation, spray, etc. The preferred formulation will depend on the intended mode of administration and therapeutic use. The pharmaceutical compositions of the present invention should be sterile and stable under the conditions of manufacture and storage. A preferred formulation is an injection. Such injection may be a sterile injectable solution. For example, the sterile injectable solution can be prepared by the following method: incorporating a necessary dose of the bispecific antibody of the invention in a suitable solvent, and optionally, incorporating other desired ingredients (including but not limited to, pH adjusting agents, surfactants, adjuvants, ionic strength enhancement agents, isotonic agents, preservatives, diluents, or any combination thereof), followed by filtration to sterilize the injectable solution. In addition, the sterile injectable solution can be prepared as sterile lyophilized powder (for example, by vacuum drying or freeze drying) to facilitate storage and use. Such sterile lyophilized powder can be dispersed in a suitable vehicle, such as sterile pyrogen-free water, before use.

Additionally, the bispecific antibody of the present invention may be presented in a pharmaceutical composition in unit dosage form for ease of administration. In certain embodiments, the unit dosage is at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg at least 30 mg, at least 45 mg, at least 50 mg, at least 75 mg, or at least 100 mg. Under the condition that the pharmaceutical composition in the form of a liquid (e.g., an injection) dosage form, it may comprise a concentration of at least 0.1 mg/ml, at least 025 mg/ml, at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml, or at least 100 mg/ml of the bispecific antibody of the present invention.

The bispecific antibody or pharmaceutical composition of the present invention may be administered by any suitable method known in the art, including, but not limited to, oral, buccal, sublingually, ocular, topical, parenteral, rectal, intrathecal, intra-cisterna, groin, intravesical, topical (e.g., powders, ointments or drops), or nasal route. However, for many therapeutic uses, the preferred route/mode of administration is parenteral administration (e.g., intravenous injection, subcutaneous injection, intraperitoneal injection, intramuscular injection). It should be appreciated that the route and/or mode of administration will vary depending on the intended purpose. In a preferred embodiment, the bispecific antibody or the pharmaceutical composition of the present invention is administered by intravenous infusion or injection.

The medicament, pharmaceutical composition or bispecific antibody provided by the present invention may be used singly or in combination, or may be used in combination with other pharmaceutically active agents (e.g., agents for an autoimmune disease or a tumor or infectious disease). In certain preferred embodiments, the bispecific antibody of the present invention is used in combination with other anti-inflammatory drugs or immunosuppressive agents to prevent and/or treat diseases associated with CTLA-4 and/or PDL-1 (e.g., an autoimmune disease or a tumor or infectious disease). Such additional pharmaceutically active agents can be administered prior to, concurrently with, or subsequent to administration of the bispecific antibody of the present invention or the pharmaceutical compositions of the invention.

The pharmaceutical compositions of the present invention may comprise a "therapeutically effective amount" or a "prophylactically effective amount" of the bispecific antibody of the present invention. "Prophylactically effective amount" means an amount sufficient to prevent, arrest, or delay a disease (for example, a disease associated with CTLA-4 and/or PDL-1). "Therapeutically effective amount" means an amount sufficient to cure or at least partially arrest a disease and its complications in a patient already suffering from the disease. The therapeutically effective amount of the bispecific antibody of the present invention may vary depending on factors such as the severity of the disease to be treated, the overall state of the patient's own immune system, the general condition of the patient such as age, weight and sex, and the manner in which the drug is administered as well as other treatments being administered concurrently, and so on.

In the present invention, the dosage regimen can be adjusted to achieve the best response (e.g., therapeutic or prophylactic response) of interest. For example, it may be administered in a single dose, may be administered multiple times over a period of time, or doses may be proportionally reduced or increased depending on the urgency of the treatment.

The typical non-limiting range of therapeutically or prophylactically effective amounts of the bispecific antibody of the present invention is 0.02-50 mg/kg, for example, 0.1-50 mg/kg, 0.1-25 mg/kg, or 1-10 mg/kg. It is noted that the dosage may vary depending on the type and severity of the condition to be treated. Additionally, a skilled person in the art should appreciate that, for any particular patient, the particular dosage regimen should be adjusted over time according to the needs of the patient and the professional evaluation of the physician; the dosage ranges given herein are only used for illustrative purposes and are not intended to limit the use or range of the pharmaceutical compositions of the present invention.

In the present invention, the test subject can be a mammal, such as human.

Detection/Diagnostic Methods and Kits

The bispecific antibody of the present invention is capable of specifically binding to CTLA-4 and/or PDL-1, thereby can be used for detecting the presence or level of CTLA-4 and/or PDL-1 in samples, and for diagnosing whether or not a subject is suffering from a disease associated with CTLA-4 and/or PDL-1 (such as an autoimmune disease or a tumor or infectious disease).

Thus, in another aspect, the present invention provides a kit comprising the bispecific antibody of the invention. In certain preferred embodiments, the bispecific antibody of the present invention carries a detectable label. In a preferred embodiment, the kit further comprises a second antibody that specifically recognizes the first antibody or scFv of the bispecific antibody in the present invention. Preferably, the second antibody further comprises a detectable label.

In the present invention, the detectable label may be any substances detectable by fluorescent, spectroscopic, photochemical, biochemical, immunological, electrical, optical or chemical means. It is particularly preferred that such labels are suitable for immunological detection (eg, enzyme-linked immunoassay, radioimmunoassay, fluorescent immunoassay, chemiluminescent immunoassay, etc.). Such labels are well known in the art and include, but are not limited to, enzymes (e.g., horseradish peroxidase, alkaline phosphatase, beta-galactosidase, urease, glucose oxidase, etc.), radionuclides (e.g., $^3$H, $^{125}$I, $^{35}$S, $^{14}$C, or $^{32}$P), fluorescent dyes (e.g., fluorescein isothiocyanate (FITC), fluorescein, tetramethylrhodamineisothiocyanate (TRITC), phycoerythrin (PE), Texas red, rhodamine, quantum dots or cyanine dyesderivatives (e.g., Cy7, Alexa 750), acridine ester compounds, magnetic beads (e.g., Dynabeads®), thermometric labels such as colloidal gold or colored glass or plastic (e.g., polystyrene, polypropylene, latex, etc.) beads, and biotin for binding to avidin modified with the above labels (e.g., streptavidin). Patents that teach the use of such labels include, but are not limited to, U.S. Pat. Nos. 3,817,837; 3,850,752; 3,939,350; 3,996,345; 4,277,437; 4,275,149, and 4,366,241 (each of which are incorporated herein by reference). The labels encompassed in the present invention can be detected by methods known in the an. For example, the radioactive labels can be detected by a photographic film or a scintillation counter, and the fluorescent labels can be detected by a photodetector for detecting the emitted light. Enzyme labels are typically detected by providing a substrate to the enzyme and detecting the reaction product produced by the action of the enzyme on the substrate. And the thermometric labels are detected by simply visualizing the colored label. In certain embodiments, a detectable label as described above can be linked to the bispecific antibody of the present invention by a linker with varying length to reduce potential steric hindrance.

In another aspect, the present invention provides a method of detecting the presence or level of CTLA-4 and/or PDL-1 in a sample, the method including the steps of using the bispecificantibody of the present invention. In a preferred embodiment, the bispecific antibody of the invention also carries a detectable label, in another preferred embodiment, the method further comprises the steps of detecting the bispecific antibody segment of the present invention by an agent with a detectable label. The method can be used for diagnostic purposes, or for non-diagnostic purposes (e.g., the sample is a cell sample, but not a sample from a patient).

In another aspect, the invention provides a method of diagnosing whether a test subject has a disease associated with CTLA-4 and/or PDL-1 (such as an autoimmune disease or a tumor or infectious disease), the method comprising: using the bispecific antibody of the present invention to detect the presence or level of CTLA4 and/or PDL-1 in a sample from the subject. In another preferred embodiment, the method further comprises the steps of detecting the bispecific antibody segment of the present invention by an agent with a detectable label.

In another aspect, use of the bispecific antibody of the present invention in the preparation of a kit is provided, wherein the kit is used for detecting the presence or level of CTLA-4 and/or PDL-1 in a sample, or for diagnosing whether a subject has a disease associated with CTLA-4 and/or PDL-1 (such as an autoimmune disease or a tumor or infectious disease).

Definition of Terms

In the present invention, unless otherwise stated, the scientific and technical terms used herein have the meanings commonly understood by those skilled in the art. Moreover, the steps involved in cell culture, biochemistry, nucleic acid chemistry, immunological experiments and the like used herein are conventional steps widely used in the corresponding fields. Meanwhile, for better understanding of the present invention, definitions and explanations of related terms are provided below.

Herein, "PDL-1" is also called "programmed death ligand 1 (Programmed death-ligand 1)", "programmed cell death ligand 1 (Programmed cell death ligand 1)", "Protein PD-L1", "PD-L", "PDL1", "PDCDL1", "hPD-L1", "hPD-L1", "CD274" and "B7-H1", which could be used interchangeably.

As used herein, the term "antibody" refers to an immunoglobulin molecule that is typically composed of two pairs of polypeptide chains (each pair having one light chain (LC) and one heavy chain (HC)). The light chain of an antibody can be classified as κ (kappa) and λ (lambda) light chain. The heavy chain can be classified as μ, δ, γ, α, or ε, and the antibody isotypes are defined as IgM, IgD, IgG, IgA, and IgE, respectively. Within the light and heavy chains, the variable and constant regions are joined by a "." region of about 12 or more amino acids, and the heavy chain also comprises a "D" region of about 3 or more amino acids. Each heavy chain consists of a heavy chain variable region (VH) and a heavy chain constant region (CH). The heavy chain constant region consists of three domains (CH1, CH2 and CH3). Each light chain consists of a light chain variable region (VL) and a light chain constant region (CL). Light chain constant region is comprised of one domain CL. The constant region of an antibody could mediate the binding of the immunoglobulin to host tissues or factors, including the binding to various cells of the immune system (e.g., effector cells) and the first component (C1q) of the classical complement system. VH and VL regions may be further subdivided into regions with hyper variability (termed complementarity determining regions (CDR)), interspersed with regions that are more conserved, termed framework regions (FR). Each VH and VL consists of three CDRs and four FRs arranged in the following order. FR1, CDR1, FR2, CDR2, FR3, CDR3, FR4 from the amino terminus to the carboxyterminus. The variable regions (VH and VL) of each heavy/light chain pairs form antigen binding sites, respectively. The assignment of amino acids to each region or domainis in accordance with the definition by Kabat, Sequences of Proteins of Immunological Interest (National Institutes of Health, Bethesda, Md. (1987 and 1991)), or Chothia&Lesk (1987) J. Mol. Biol.: 901-917; Chothia et al. (1989) Nature 342: 878-883.

As used herein, the term "complementarity determining region" or "CDR" refers to amino acid residues in the variable regions of an antibody that are responsible for antigen binding, which generally could include residues in the light chain variable region, 24-34 {LCDR1}, 50-56 {LCDR2}, 89.97 {LCDR3} and residues in the heavy chain variable region, 31-35 {HCDR1}, 50-65 {HCDR2}, 95-102 {HCDR3}(See, for example, Kabat et al., Sequences of Proteins of Immunological Interest, Fifth Edition, Public Health Service, National Institutes of Health, Bethesda, Md. (1991)), or residues in the light chain variable region, 26-32 {L1}, 50-52 {L2}, 91-96 {L3} and residues in the heavy chain variable region, 26-32 {H1}, 53-55 {H2}, 96-101 {H3} (See, Chothia and Lesk J. Mol. Biol. 196: 901-917 (1987)). Alternatively, CDRs could be obtained by techniques that are well known to a skilled person in the art, for example, by analyzing the amino acid sequence of the heavy chain variable region or the amino acid sequence of the light chain variable region according to the IMGT definition through the VBASE2 database.

As used herein, the term "framework region" or "FR" residues refers to those amino acid residues in the variable regions of an antibody other than the CDR residues as defined above.

The term "antibody" is not limited by any particular method of making an antibody. For example, it includes recombinant antibody, monoclonal antibody, and polyclonal antibody. The antibodies may be antibodies of different isotypes, for example, IgG (eg, IgG1, IgG2, IgG3 or IgG4 subtype), IgA1, IgA2, IgD, IgE or IgM antibody.

As used herein, the term "antigen binding site" refers to the portions that are formed by amino acid residues of the heavy and light chain variable regions (VH and VL) and are used to participate in antigen binding, including those amino acid residues that interact with an antigen and determine its specificity and affinity for the antigen. The antigen binding site also could comprises amino acid residues of the framework regions, which are necessary for maintaining the proper conformation of the amino acid residues directly binding to the antigen described above.

As used herein, the term "full length antibody" means an antibody consisting of two "full length heavy chains" and two "full length light chains". A "full-length heavy chain" refers to a polypeptide chain which is composed of a heavy chain variable region (VH), a heavy chain constant region CH1 domain, a hinge region (HR), a heavy chain constant region CH2 domain and a heavy chain constant region CH3 domain in the direction from N-terminus to C-terminus. When the full length antibody belongs to the IgE isotype, it optionally further comprises a heavy chain constant region CH4 domain. Preferably, the "full length heavy chain" is a polypeptide chain consisting of VH, CH1, HR, CH2 and CH3 from its N-terminus to C-terminus. The "full length light chain" is a polypeptide chain consisting of a light chain variable region (VL) and a light chain constant region (CL) from its N-terminus to C-terminus. Two pairs of full length antibody chains are joined by a disulfide bond between CL and CH1 and a disulfide bond between the HRs of the two full length heavy chains. The full length antibodies of the present invention may be from a single species, such as human; or may be chimeric or humanized antibodies. The full-length antibody of the present invention comprises two antigen-binding sites each formed by a pair of VH and VL, respectively. The two antigen-binding sites specifically recognize/bind the same antigen.

As used herein, the term "Fab fragment" means an antibody fragment consisting of the VL, VH, CL and CH1 domains. The term "Fab' fragment" means a fragment obtained by reducing the disulfide bond of two heavy chain fragments in a F(ab')$_2$ fragment and consists of a complete light chain and the Fd fragment of heavy chain (formed by VH and CH1 domains). The term "F(ab')$_2$ fragment" means an antibody fragment comprising two Fab fragments joined by a disulfide bridge on the hinge region. Each of the above antibody fragments retains the ability to specifically bind to the same antigen to which the full length antibody binds, and/or compete with the full length antibody for specific binding to the antigen.

As used herein, the term "scFv" refers to a single polypeptide chain comprising VL and VH domains, wherein the VL and VH are linked by a linker (See, for example, Bird et al, Science 242: 423-426 (1988); Huston et al, Proc. Natl. Acad. Sci. USA 85: 5879-5883 (1988); and Pluckthun, The Pharmacology of Monoclonal Antibodies, Volume 113, edited by Roseburg and Moore, Springer-Verlag, New York, pp. 269-315 (1994)). Such scFv molecules can have the general structure: NH$_2$-VL-linker-VH—COOH or NH$_2$—VH-linker-VL-COOH. A disulfide bond could also be present between VH and VL of the scFv of the present invention. Methods for introducing a disulfide bond between VH and VL of an antibody are well known in the art. See, for example, U.S. Pat. No. 5,747,654; Rajagopal et al, Prot. Engin. 10 (1997) 1453-1459; Reiter et al, Nature Biotechnology 14 (1996) 1239-1245; Reiter et al, Protein Engineering 8 (1995) 1323-1331; Webber et al, Molecular Immunology 32 (1995) 249-258; Reiter et al, Immunity 2 (1995) 281-287; Reiter et al. JBC 269 (1994) 18327-18331; Reiter et al, Inter. J. of Cancer 58 (1994) 142-149; or, Reiter et al, Cancer Res. 54 (1994) 2714-2718; which are incorporated herein by reference. As used herein, the term "di-scFv" refers to an antibody fragment formed by joining two scFvs.

As used herein, the term "Fv fragment" means an antibody fragment consisting of the VL and VH domains of a single arm of an antibody.

As used herein, the term "parental antibody" refers to an anti-PDL-1 antibody or an anti-CTLA-4 antibody used to prepare the bispecific antibody of the present invention. The amino acid sequence of the parental antibody can be subjected to for example, amino acid substitution or structural alteration or the like in order to prepare the first antibody or scFv comprised by the bispecific antibody of the invention.

The CDR, VH, VL, CH, CL, HC, LC of the bispecific antibody of the present invention, can also be derived from other antibodies or antibody fragments thereof which are known in the art to specifically bind to PDL-1 or CTLA-4, or from antibodies that have a sequence identity of at least 90%, at least 91%, at least 92%, at least 93%, at least 94%, at least 95%, at least 96%, at least 97%, at least 98%, at least 99%, or 100% to the above-mentioned known antibodies, antibody fragments thereof or the CDR, VH, VL, CH, CL, HC, LC thereof.

As used herein, the term "linker" refers to a linear polypeptide formed by joining of multiple amino acid residues by peptide bonds. The linker of the invention may be a synthetic amino acid sequence, or a naturally occurring polypeptide sequence, such as a polypeptide having the function of a hinge region. Such linker polypeptides are well known in the art (see, for example, Holliger, P. et al. (1993) Proc. Natl. Acad. Sci. USA 90:6444-6448; Poljak, R J et al. (1994) Structure 2:1121-1123)).

As used herein, the term "specifically binds" refers to a non-random binding reaction between two molecules, such as a reaction between an antibody and the antigen to which it is directed. In certain embodiments, an antibody that specifically binds to an antigen (or an antibody that is specific for an antigen) means that the antibody binds to the antigen with an affinity ($K_D$) of less than about $10^{-5}$ M, for example less than about $10^{-6}$ M, $10^{-7}$ M, $10^{-8}$ M, $10^{-9}$ M or $10^{-10}$ M or lesser. In the present invention, the term "$K_D$" refers to the dissociation equilibrium constant of a particular antibody-antigen interaction, which is used to describe the binding affinity between an antibody and an antigen. The smaller the dissociation equilibrium constant, the tighter the antibody-antigen binding and the higher the affinity between the antibody and the antigen. Typically, an antibody (e.g., an antibody of the present invention) binds to an antigen (e.g., HBsAg) with a dissociation equilibrium constant ($K_D$) of less than about $10^{-5}$ M, for example less than about $10^{-6}$ M, $10^{-7}$ M, $10^{-8}$ M, $10^{-9}$ M or $10^{-10}$ M or less affinity. For example, $K_D$ is measured by surface plasmon resonance (SPR) in a BIACORE instrument.

As used herein, the term "vector" refers to a nucleic acid vehicle into which a polynucleotide can be inserted. A vector is referred to as an expression vector when the vector enables expression of the protein encoded by the inserted polynucleotide. The vector can be introduced into a host cell by transformation, transduction or transfection, and thereby the genetic material element carried therein can be expressed in the host cell. Vectors are well known to a skilled person in the art and include, but are not limited to: plasmid; phagemid; cosmid, artificial chromosome, such as yeast artificial chromosome (YAC), bacterial artificial chromosome (BAC) or P1 derived artificial chromosome (PAC); phage such as lambda phage or M13 phage and animal virus. Animal viruses used as vectors include, but are not limited to, retroviruses (including lentiviruses), adenoviruses, adeno-associated viruses, herpes viruses (such as herpes simplex virus), poxviruses, baculoviruses, papillomaviruses, papovavirus (such as SV40). A vector may contain a variety of elements that control expression, including, but not limited to, promoter sequences, transcription initiation sequences, enhancer sequences, selection elements, and reporter genes. In addition, the vector may also contain an origin of replication.

As used herein, the term "host cell" refers to a cell to which that a vector can be introduced, including but not limited to, prokaryotic cells such as *Escherichia coli* or *Bacillus subtilis*, fungal cells such as yeast cell or *Aspergillus*, insect cells such as S2 *Drosophila* cell or Sf9, or animal cells such as fibroblast, a CHO cell, a COS cell, a NS0 cell, a HeLa Cell, a BHK cell, a HEK 293 cell or a human cell.

As used herein, the term "identity" is used to mean the matching of sequences between two polypeptides or between two nucleic acids. When a position in the two sequences being compared is occupied by the same base or amino acid monomer submit (for example, a position in each of two DNA molecules is occupied by adenine, or a position in each of the two polypeptides is occupied by lysine), then the molecules are identical to each other at that position. The "percent identity" between the two sequences is a function, obtained by the number of matching positions shared by the two sequences divided by the number of positions to be compared×100. For example, if 6 of the 10 positions in the two sequences match, then the two sequences have 60% identity. For example, the DNA sequences CTGACT and CAGGTT share 50% identity (3 out of a total of 6 positions match). Typically, the comparison is made when the two sequences are aligned to produce maximum identity. Such an alignment can be conveniently accomplished by using, for example, a computer program such as the Align program (DNAstar, Inc.) to perform the methods in Needleman et al. (1970) J. Mol. Biol. 48:443-453. The algorithm of E. Meyers and W. Miller (Comput. ApplBiosci., 4:11-17 (1988)), which is integrated into the ALIGN program (version 2.0), can also be used to determine the percent identity between two amino acid sequences by using the PAM120 weight residue table, a gap length penalty of 12 and a gap penalty of 4. In addition, the Needleman and Wunsch (J Mol Biol. 48:444-453 (1970)) algorithms, which are integrated into GAP program of the GCG package (available at www.gcg.com) can be used to determine the percentage identity between two amino acid sequences by using the Blossum 62 matrix or the PAM250 matrix, the gap weight of 16, 14, 12, 10, 8, 6 or 4 and the length weight of 1, 2, 3, 4, S or 6.

The writing of the twenty conventional amino acids involved herein follows conventional usage. See, for example, Immunology-A Synthesis (2nd Edition, E. S. Golub and D. R. Gren, Eds., Sinauer Associates, Sunderland, Mass. (1991)), which is incorporated herein by reference. In the present invention, the terms "polypeptide" and "protein" have the same meaning and are used interchangeably. Additionally, in the present invention, amino acids are generally represented by single letter and three letter abbreviations as well known in the an. For example, alanine can be represented by A or Ala.

The term "pharmaceutically acceptable carrier and/or excipient" as used herein refers to a carrier and/or excipient that is pharmacologically and/or physiologically compatible with the subject and the active ingredient, which is well known in the field (see, e.g. Remington's Pharmaceutical Sciences Edited by Gennaro A R, 19th ed Pennsylvania: Mack Publishing Company, 1995) and includes but is not limited to, pH adjusters, surfactants, adjuvants, ionic strength enhancers, diluents, osmotic pressure maintaining agents, delayed absorption agents, preservatives. For example, pH adjusting agents include, but are not limited to, phosphate buffers. Surfactants include, but are not limited to, cationic, anionic or nonionic surfactants such as Tween-80. Ionic strength enhancers include, but are not limited to, sodium chloride. Preservatives include, but are not limited to, various antibacterial and antifungal agents, such as parabens, chlorobutanol, phenol, sorbic acid, and the like. Osmotic pressure maintaining agents include, but are not limited to, sugars, NaCl, and the like. Delayed absorption agents include, but are not limited to, monostearate and gelatin.

As used herein, the term "subject" refers to a mammal, such as a primate mammal, such as a human. In certain embodiments, the subject (e.g., a human) has a disease associated with CTLA-4 and/or PDL-1, or has a risk of suffering from the above-described disease. In general, the characteristics of such diseases or disease states are that a subject with the diseases or disease states will benefit from a decrease of CTLA-4 and/or PDL-1 level or inhibition of CTLA-4 and/or PDL-1 activity, and thus the diseases or disease states will be reliefed or cured.

As used herein, the term "effective amount" refers to an amount sufficient to achieve, or at least partially achieve a desired effect. For example, the effective amount to prevent a disease (e.g., a disease associated with CTLA-4 and/or PDL-1) is the amount that is sufficient to prevent, arrest, or delay the occurrence of a disease (e.g., a disease associated with CTLA-4 and/or PDL-1); the effective amount to treat a disease is the amount that is sufficient to cure or at least partially prevent the disease and its complications in a patient who has already suffered from the disease. Determinating such an effective amount is well within the skill of the art. For example, the effective amount for therapeutic use will depend on the severity of the condition to be treated, the overall condition of the patient's own immune system, the general condition of the patient such as age, weight and sex, the administration mode of the drug, as well as other treatments being administered concurrently or the like.

As used herein, the term "antibody-dependent cell-mediated cytotoxicity (ADCC)" refers to a cytotoxic form, in which Ig binds to Fc receptors (FcR) present on cytotoxic cells such as natural killer (NK) cells, neutrophils or macrophages, resulting in the cytotoxic effector cells specifically binding to the target cells to which the antigen is attached and killing the target cells by secretion of the cytotoxin. Methods for detecting the ADCC activity of an antibody are known in the art, for example, by measuring the binding activity between an antibody to be tested and an Fc receptor (e.g., CD16a).

As used herein, the term "complement dependent cytotoxicity (CDC)" refers to a cytotoxic form in which the complement cascade is activated by the binding of complement component C1q to antibody Fc. Methods of detecting the CDC activity of an antibody are known in the art. For example, the CDC activity can be evaluated by measuring the binding activity between an antibody to be tested and an Fc receptor (e.g., C1q).

Advantageous Effects of the Present Invention

Compared with the prior art, the technical solution of the present invention has at least the following advantageous effects:

The bispecific antibody of the present invention not only specifically recognize/bind CTLA-4 and PDL-1, but also has affinities for CTLA-4 and PDL-1 comparable to that of its respective parental antibodies, or has weaker affinities for CTLA-4 than that of its parental antibody. The bispecific antibodies in the present invention can significantly and simultaneously inhibit the activities of CTLA-4 and/or PDL-1 and block the CTLA-4 and/or PDL-1 signaling pathways in vitro and in test subjects. Furthermore, the bispecific antibody of the present invention has an excellent thermal stability equivalent to that of the parental antibody of the first antibody. It is particularly surprising that in some cell-level and in vivo experiments, the bispecific antibody of the present invention exhibits a significant greater inhibitory activity and a reduced antibody toxicity than their parental antibodies, thus increasing the safety of the drug. Therefore, the bispecific antibody of the present invention has a potential for treating a disease associated with CTLA-4 and PDL-1 (such as an autoimmune disease or a tumor or infectious disease), and has a great clinical value.

The embodiments of the present invention will be described in details below with reference to the accompanying figures and examples. However, a skilled person in the art will understand that the following figures and examples are merely used to illustrate the present invention and are not intended to limit the scope of the present invention. According to the following detailed description of the figures and preferred embodiments, various objects and advantages of the present invention will become practicable to the skilled person in the art.

SEQUENCE INFORMATION

Figure 1:
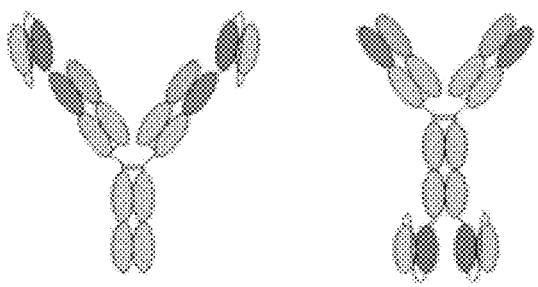
FIG. 1 shows a diagram of the structures of anti-PDL-1 and CTLA-4 recombinant bispecific antibodies AB03 and AB04.

Partial sequence information associated with the present invention is provided in Table 1.

TABLE 1

| SEQ ID NO: | Sequence name/description |
|---|---|
| 1 | AB01 HCDR1 |
| 2 | AB01 HCDR2 |
| 3 | AB01 HCDR3 |
| 4 | AB01 LCDR1 |
| 5 | AB01 LCDR2 |
| 6 | AB01 LCDR3 |
| 7 | AB01 VH |
| 8 | AB01 mutant VH |
| 9 | AB01 VL |
| 10 | AB01 mutant VL |
| 11 | AB01 light chain |
| 12 | AB01 heavy chain |
| 13 | AB02 HCDR1 |
| 14 | AB02 HCDR2 |
| 15 | AB02 HCDR3 |
| 16 | AB02 LCDR1 |
| 17 | AB02 LCDR2 |
| 18 | AB02 LCDR3 |
| 19 | AB02 VH |
| 20 | AB02 mutant VH |
| 21 | AB02 VL |
| 22 | AB02 mutant VL |

TABLE 1-continued

| SEQ ID NO: | Sequence name/description |
|---|---|
| 23 | AB02 light chain |
| 24 | AB02 heavy chain |
| 25 | S2 |
| 26 | S1 |
| 27 | S1 |
| 28 | AB03 first polypeptide chain amino acid sequence |
| 29 | AB04 first polypeptide chain amino acid sequence |
| 30 | IgG-Kappa signal peptide amino acid |
| 31 | AB01-scFv amino acid sequence* |
| 32 | AB02-scFv amino acid sequence* |

*Note:
AB01-scFv represents scFv derived from the parental antibody AB01, which differs from AB01 in variable regions by that: the amino acids at the position 44 of be VH and the position 100 of the VL of the scFv are cysteine respectively. AB02-scFv represents scFv derived from the parental antibody AB02, which differs from AB02 in variable regions in that: the amino acids at the position 44 of the VH and the position 100 of the VL of the scFv are cysteine respectively. Other similar expressions have similar meanings.

DETAILED DESCRIPTION OF EMBODIMENTS

The present invention will now be described with reference to the following examples, which are intended to illustrate (but not to limit) the present invention.

Unless otherwise indicated, molecular biological experimental methods and immunodetection methods used in the present invention are performed basically by referring to J Sambrook et al., Molecular Cloning: a laboratory manual, the second edition, Cold Spring Harbor Laboratory Press, 1989, and F/M Ausubel et al., Short Protocols in Molecular Biology, 3 rd edition, John Wiley and Sons, Inc., 1995. The use of the restriction endonuclease is in accordance with the conditions recommended by the product manufacturer. As known by those skilled in the art, the embodiments describe the present invention by way of examples, and are not intended to limit the scope of protection claimed by the present invention.

Example 1. Construction of Expression Vectors for Encoding Anti-PDL-1CTLA4 Recombinant Bispecific Antibody In this example, the anti-CTLA-4 parental antibody (AB02) shown in Table 2 was purchased from Bristol-Myers Squibb. Firstly, the anti-PDL-1 parental antibody (AB01) shown in Table 2 was obtained through DNA recombination technology, then an expression vector containing the nucleotide sequence encoding the first polypeptide chain and an expression vector containing the nucleotide sequence encoding the second polypeptide chain were constructed respectively to obtain the recombinant antibodies AB03 and AB04 of the present application.

The variable region and constant region sequences of each of the parental antibody AB01 and AB02 were shown in table 2. The encoding nucleic acid sequence of the parental antibody (AB01) was synthesized by Genscript (Nanjing) in a format of whole gene, and then cloned into the a PUC19 vector.

TABLE 2

Variable and constant region sequences of parental antibodies and PDL-1/CTLA-4 recombinant bispecific antibodies

| Parental anitibody | Corresponding antigen | Light chain variable region (SEQ ID NO:) | Heavy chain variable region (SEQ ID NO:) | Light chain constant region (database accession number) | Heavy chain constant region (database accession number) |
|---|---|---|---|---|---|
| AB01 | PDL-1 | 9 | 7 | UniProt P01834 | The positions 117, 118, and 120 of the Uniport P01857 are A |
| AB02 | CTLA-4 | 21 | 19 | UniProt P01834 | The position 97 of the Uniprot P-1857 is R |

*Note:
database accession mmiber is Uniprot number.

The nucleotide sequence for encoding the first polypeptide chain of recombinant antibody and the nucleotide sequence for encoding the second polypeptide chain were constructed according to construction mode of each recombinant antibody as shown in Table 3. For scFv in each recombinant antibody, the VL and the VH of scFv were linked through a peptide linker S2 (SEQ ID NO: 25, the amino acid sequence is: GGGGSGGGGSGGGGSGGGGS), and the amino acids at the position 44 of the VH in the parental antibody of the scFv and the position 100 of the VL in the parental antibody of the scFv were respectively mutated into cysteine (Cys, C) by PCR site-directed mutagenesis, so that a disulfide bond was formed between VH and VL of the scFv. The amino acid sequence of the mutated AB01-scFv was set forth in SEQ ID NO: 31, the amino acid sequence of the mutated VL was set forth in SEQ ID NO: 10, and the amino acid sequence of the mutated VH was set forth in SEQ ID NO: 8. The amino acid sequence of the mutated AB02-scFv was set forth in SEQ ID NO: 32; the amino acid sequence of the mutated VL was set forth in SEQ ID NO: 22; and the amino acid sequence of the mutated VH was set forth in SEQ ID NO: 20.

The construction modes of recombinant antibodies as shown in table 3 were exemplarily presented in FIG. 1

TABLE 3

Construction of each recombinant antibody

| Bispecific antibody | First polypeptide chain | | | Second polypeptide chain | Structure of scFv | Linker S2(SEQ ID NO:) |
|---|---|---|---|---|---|---|
| | N-terminus | Linker S1(SEQ ID NO:) | C-terminus | | | |
| AB03 | AB02-scFv | 26 | VH of AB01 linked to constant region of UniProt P01857 | Light chain of AB01 | VL-S2-VH | 25 |

TABLE 3-continued

Construction of each recombinant antibody

| Bispecific antibody | First polypeptide chain | | | Second polypeptide chain | Structure of scFv | Linker S2(SEQ ID NO:) |
|---|---|---|---|---|---|---|
| | N-terminus | Linker S1(SEQ ID NO:) | C-terminus | | | |
| AB04 | VH of AB01 linked to constant region of UnitProt P01857 | 27 | AB02-scFv | Light chain of AB01 | VL-S2-VH | 25 |

Specifically, nucleic acid constructs for the exemplary recombinant antibodies were constructed as follows:

The nucleotide sequence encoding AB02-scFv was linked to the 5' end of the nucleotide sequence encoding VH of AB01 by nucleotide sequence encoding a linker S1 set forth in SEQ ID NO:26, and then linked to the 5' end of the nucleotide sequence encoding the heavy chain constant region of UniProt P01857 so as to construct the nucleotide sequence encoding the first polypeptide chain of AB03. The domain order of AB02-scFv from the N-terminus to the C-terminus was VL-S2-VH, the encoded amino acid sequence was set forth in SEQ ID NO: 32.

The nucleotide sequence encoding AB01 light chain served as the nucleotide sequence encoding the second polypeptide chain of AB03.

The nucleotide sequence of AB01 VH was linked to the 5' end of the nucleotide sequence encoding the heavy chain constant region of Uniprot P11857, and then linked to the 5' end of the nucleotide sequence enlcoding AB02-scFv by nucleotide sequence encoding a linker S1 set forth in SEQ ID NO: 27, forming a nucleotide sequence encoding the first polypeptide chain of AB04. The domain order of AB02-scFv from the N-terminus to the C-terminus was VL-S2-VH, and the encoded amino acid sequence was set forth in SEQ ID NO: 32.

The nucleotide sequence encoding AB01 light chain served as the nucleotide sequence encoding the second polypeptide chain of AB04.

The nucleotide sequence encoding the first polypeptide chain or second polypeptide chain above was linked to the nucleotide sequence encoding the IgG-kappa signal peptide (the amino acid sequence of SEQ ID NO: 30), and was respectively introduced into the pTT5 plasmid by means of homologous recombination, so as to construct an pTT5 expression vector for encoding the first polypeptide chain and encoding the second polypeptide chain. The amino acid sequence of each recombinant antibody finally obtained was shown in Table 4.

Example 2. Expression of Anti-PDL-1/CTLA-4 Recombinant Bispecific Antibodies The well grown CHO-S cells (Thermo Fisher, catlog No. A1155701) in logarithmic phase were centrifuged and resuspend in 250 ml of CHOgro culture medium (purchased from Mirus Corporation) with a final density $3.5*10^6$ cells/ml. Plasmids obtained in Example 1 to be used for transfection were sterilized by filtering with a 0.22 μm filter membrane. 125 μg of recombination plasmid of the first polypeptide chain and 125 μg recombination plasmid of a corresponding second polypeptide chain were added into 25 ml of CHOgro complex formation solution (purchased from Mirus Corporation), to which 1.25 ml of PEIMAX (purchased from Polysciencs Corporation) at 1 mg/ml was added, mixed with shaking for three times, stranded for 10 minutes, then added to 250 ml of the cell culture. The culture was placed in a shaker at 37° C. and 5% $CO_2$ for 24 hours, and 20 ml of 10% Sheff-CHO PF ACF (purchased from Kerry Corporation) was added. The culture was continued for additional 7 days, and then collected.

Example 3. Purification of Anti-PDL-1/CTLA-4 Recombinant Bispecific Antibodies Take the CHO-S cell culture already expressed for 7 days in example 2 firstly centrifuged at a low speed to separate the supernatant from the cell precipitate; and then centrifuged at a high speed to obtain a clear material liquid. The recombinant antibody was purified by means of an affinity chromatography method (Protein A) and an ion exchange method, and the purification resin used were MAB Select Sure produced by GE Corporation and Eshmuno CPX produced by Millipore Corporation respectively. The expression yield of each recombinant bispecific antibody was substantially consistent, within the range of 40-85 mg/L, and the expression level was consistent with that of the anti-PDL-1 parental antibody AB01 under the same

TABLE 4

Amino acid sequences of each recombinant antibody

Figure 2:
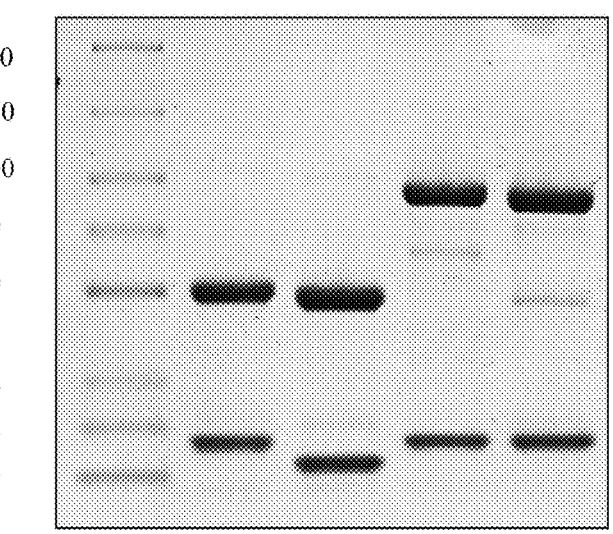
FIG. 2 shows a reduced SDS-PAGE of AB03 and AB04, and from left to right lanes: reduced AB01, reduced AB02, reduced AB03, reduced AB04.

| Recombinant antibody | First antibody(SEQ ID NO:) | | ScFv(SEQ ID NO:) | | First polypeptide chain(SEQ ID NO:) | Second polypeptide chain(SEQ ID NO:) |
|---|---|---|---|---|---|---|
| | VH | VL | VH | VL | | |
| AB03 | 7 | 9 | 20 | 22 | 28 | 11 |
| AB04 | 7 | 9 | 20 | 22 | 29 | 11 | condition. This indicated that each recombinant antibody could be successfully expressed, and had high expression efficiency. The specific expression level of each recombinant antibody was shown in Table 5. The isolated and purified recombinant antibody was concentrated by means of an ultrafiltration tube, and then dissolved in PBS solution. A reduced SDS-PAGE was shown in FIG. 2, in which AB01 and AB02 had sizes of 50 kDa (heavy chain) and 25 kDa (light chain), respectively after being reduced; The reduced bands of the bispecific antibodies AB03 and AB04 had sizes of 75 kDa (first peptide chain) and 25 kDa (second peptide chain) respectively, and the SEC purities of the two antibodies AB03 and AB04 were 96.34% and 96.04%, respectively. The sizes of the bands were consistent with those expected for the antibodies, indicating that all the recombinant bispecific antibodies could be expressed efficiently and correctly assembled. Obvious aggregation and degradation did not exist, which indicated that the stability of the recombinant bispecific antibodies was good.

TABLE 5

Expression level of recombinant bispecific antibodies

| Antibody name | Amount of protein obtained | Expression yield |
|---|---|---|
| AB01 | 20.5 mg | 60 mg/L |
| AB03 | 22.6 mg | 83 mg/L |
| AB04 | 12.2 mg | 42 mg/L |

Example 4. Detection of Antigen Binding Activity of Anti-PDL-1/CTLA-4 Recombinant Bispecific Antibody In the present example, affinity difference between each recombinant bispecific antibodies and their parental antibodies in binding to the same antigens, and the relative affinity of the recombinant bispecific antibodies binding to both antigens were measured in an ELISA manner, in order to verify whether the ability to block a single antigen of the recombinant bispecific antibodies was lower than those of the parental antibodies, and whether both of two antigens or two signal pathways could be blocked so as to generate a synergistic effect.

4.1 PDL-1 Binding Activity Detection of the Recombinant Bispecific Antibodies

Figure 3:
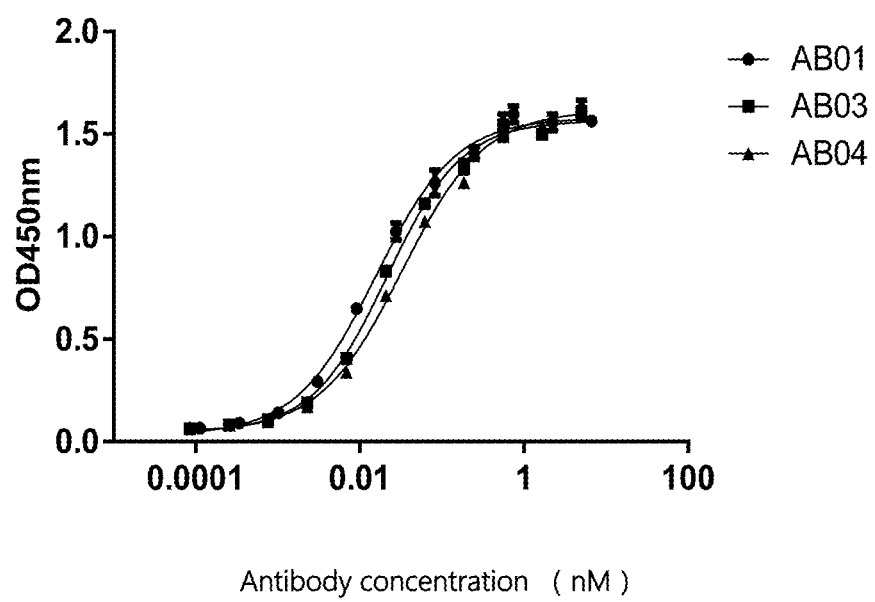
FIG. 3 shows binding activity curves of antibodies to PDL-1.

The recombinant PDL-1-mFc protein (obtained from Kelun-Biotech, Uniport No.: Q9NZQ7) was added into a 96-well enzyme labeled plate (purchased from Thermo) at 100 ng/well, and coating was carried out at 4° C. overnight. On the next day, the solution in the wells was discarded, and the wells were washed with a washing buffer (a phosphate buffer solution containing 0.05% Tween-20) for one time and the solution in the wells was discarded. PBS solution containing 2% BSA was added at 100 μl/well and the wells were blocked at 3'C for 2 hours. Then the solution in the well was discarded. The recombinant bispecific antibodies AB03 and AB04 and the parental antibody AB01 were diluted in 3 folds serially at a start concentration of 1000 ng/mL to get 11 concentration gradients, and were added to the well at 100 μl/well. The plate was incubated at 37° C. for 2 hours, then the solution in the wells was discarded and the wells were washed for three times. HRP conjugated goat anti-human IgG(H+L) was added into the plate at 100 μl/well and the plate was incubated at 37° C. for 1 hour. TMB solution was added to the wells at a concentration of 100 μl/well, and the reaction was carried out at room temperature for about 5 minutes. A stop solution at 100 μl/well was added to the plate, and then the plate was put into an ELISA plate reader reading OD450 absorbance values. A fitting curve was made by the means of the experimental data, as shown in FIG. 3, and EC50 was calculated.

The EC50 result presented in Table 6 showed that the binding activity EC50 of the recombinant bispecific antibody to the PDL-1-mFc was equivalent to that of the parental antibody AB01 against the PDL-1-mFc, indicating that the recombinant antibody of the present invention maintained the same excellent binding activity to PDL1-mFc as that of the parental antibody overall.

TABLE 6

Binding activity of recombinant antibodies to PDL-1-mFc

| Recombinant/ parental antibody | EC50(pM) |
|---|---|
| AB01 | 15.55 |
| AB03 | 21.46 |
| AB04 | 32.43 |

4.2 Detection of Binding Activities of Recombinant Bispecific Antibodies to CTLA-4

Figure 4A:
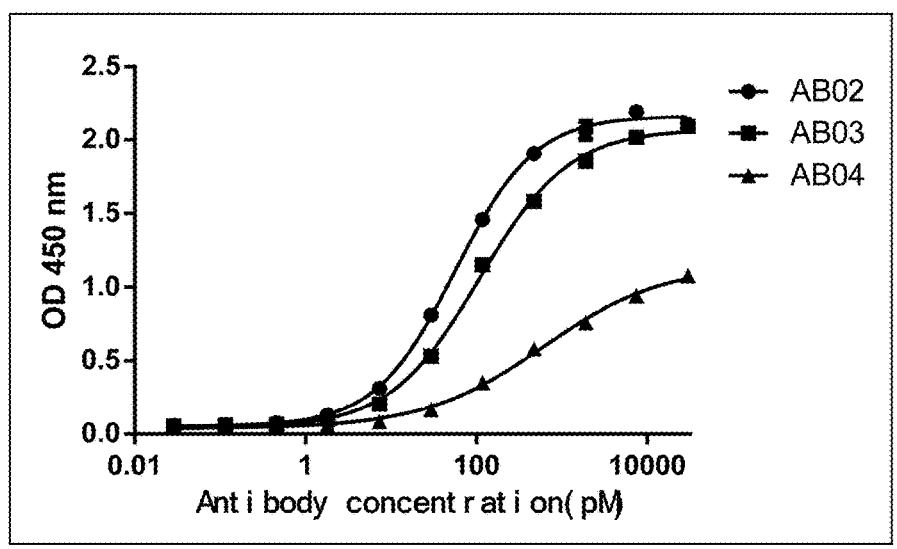
FIG. 4A and FIG. 4B in FIG. 4 show binding activity curves of antibodies to different batches of CTLA4.
Figure 4B:
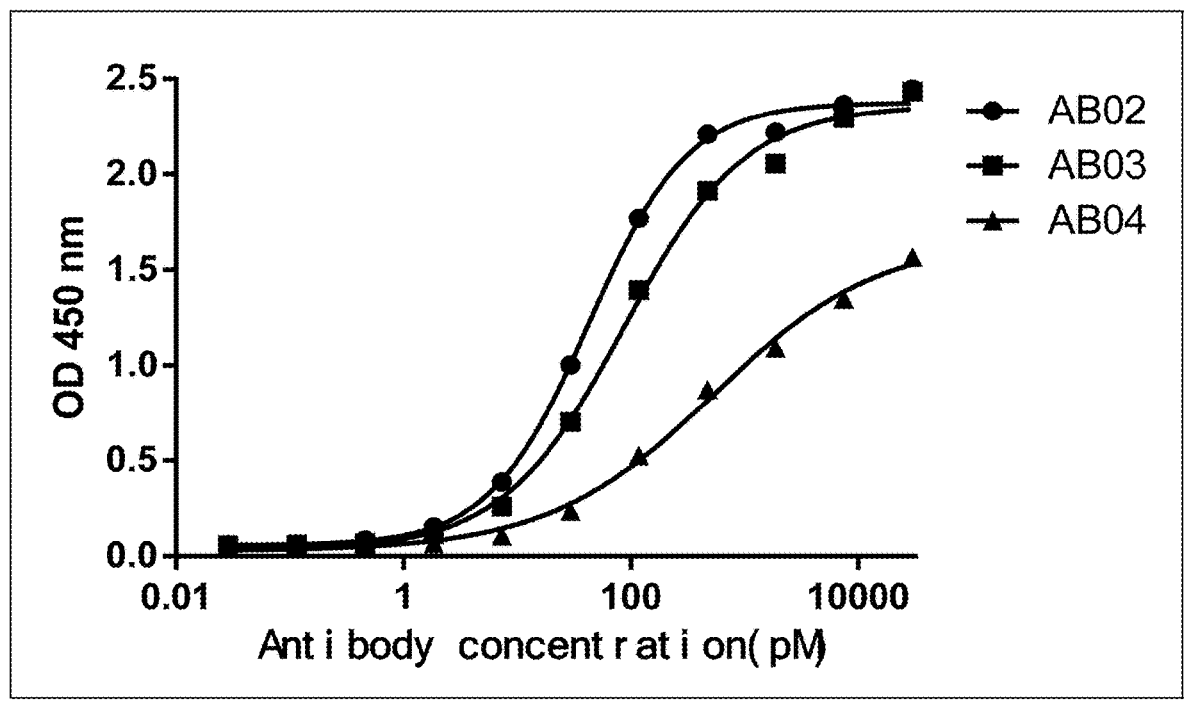

Two batches of recombinant CLTA-4-His proteins (obtained from Kelun-Biotech, Uniport No.: P16410) were diluted with PBS respectively, the dilutes of CTLA-4-His at 100 μl/well were added into a 96-well ELISA plate, and coating was carried out at 4° C. overnight. On the next day, the solution in the wells was discarded, and wells were washed one time with washing buffer and the solution in the wells was discarded again. PBS solution containing 2% BSA was added at 100 μl/well for blocking the well at 37° C. for 2 hours, and then the solution in the well was discarded. The recombinant bispecific antibodies AB03 and AB04 and anti-CTLA-4 parental antibody AB02 were diluted 4 folds serially at a start concentration of 30 nM, to get 11 concentration gradients, and were added to the wells at 100 μl/well. The HRP conjugated goat anti-human IgG (H+L) solution was added into the plate and the plate was incubated at 37° C. for 1 hour. TMB solution was added to the well, and the reaction was carried out at room temperature for about 8 minutes. The stop solution was added to the plate, and then the plate was put into an ELISA plate reader to read OD450 absorbance values. Fitting curves were made by the means of the experimental data, as shown in FIG. 4A and FIG. 4B, and EC50 was calculated.

The EC50 result was shown in Table 7.

TABLE 7

The binding activity of the recombinant antibody to CTLA-4

| CLTA-4-His protein batch No. Recombinant/parental anitbody | Batch 1 EC50(pM) | Batch 2 EC50(pM) |
|---|---|---|
| AB02 | 55.93 | 42.38 |
| AB03 | 107.5 | 86.17 |
| AB04 | 600.2 | 531.3 |

According to the experimental results, the EC50 of the recombinant bispecific antibody AB03 binding to CTLA-4 was slightly increased compared with that of the parental antibody AB02, and the EC50 of the recombinant bispecific antibody AB4 binding to CTLA-4 was about 10 to 12 times of that of the parental antibody AB02. It indicated that the binding activity of AB04 to CTLA-4 was obviously weaker than that of the parental antibody, but still had an efficient binding activity of pM level.

Figure 5:
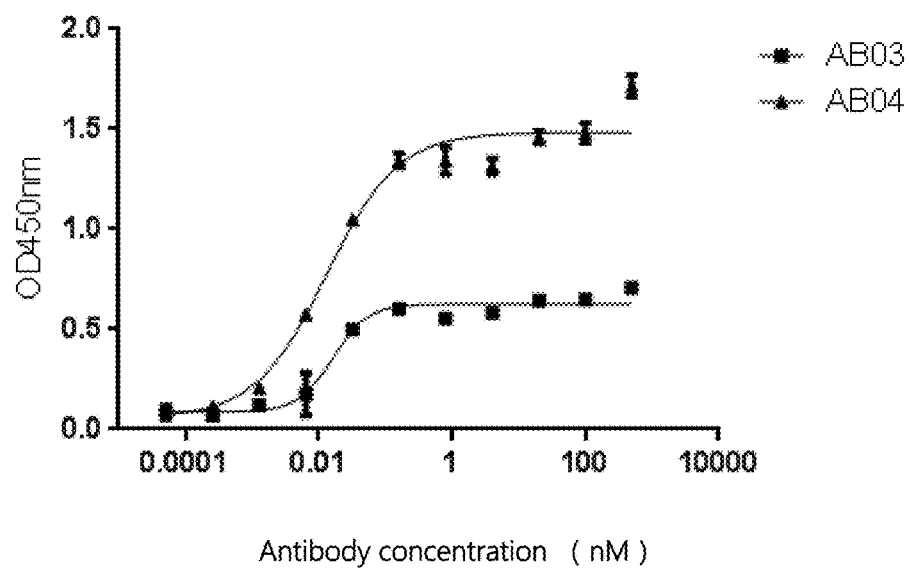
FIG. 5 shows binding activity curves of antibodies to PDL-1 and CTLA-4 simultaneously.

4.3 Detection of Binding Activities of Recombinant Bispecific Antibodies to PDL-1 and CTLA-4 Simultaneously The recombinant PDL-1-mFc protein (obtained from Kelun-Biotech, Uniport No: Q9NZQ7) was added into a 96-well enzyme labeled plate (purchased from Thermo) at 100 ng/well, and coating was carried out at 4° C. overnight. On the next day, the solution in the wells was discarded, wells were washed one time with washing buffer (phosphate buffer solution containing 0.05% Tween-20) and solution in the well was discarded again. PBS solution containing 2% BSA was added at 100 μl/well for blocking the wells at 37° C. for 2 hours, and then solution in the wells was discarded. The recombinant bispecific antibodies were diluted 5 folds serially at a start concentration of 100000 ng/mL to get 11 concentration gradients, and were added to the wells at 100 μl/well. The plate was incubated at 37° C. for 2 hours, then the solution in the wells was discarded and wells were washed with the washing buffer for three times. 1.5 ug/ml of the CTLA-4-His protein was added into the plate at 100 μl/well, and plate was incubated at 37° C. for 2 hours. Then the solution in the wells was discarded and wells were washed with the washing buffer for three times. HRP conjugated goat anti-his (purchased from BioLegend) was added into the plate and the plate was incubated at 37° C. for 1 hour. TMB solution was added to the wells, and the reaction was carried out at room temperature for about 5 minutes. Stop solution was added to the plate, and then the plate was put into an ELISA plate reader to read OD450 absorbance values. A fitting curve was made by the means of the experimental data, as shown in FIG. 5, and EC50 was calculated.

The EC50 result was shown in Table 8. The EC50 values of the recombinant bispecific antibodies AB03 and AB04 to both the PDL-1 and the CTLA-4 antigens were at pM levels. The above results showed that after the recombinant bispecific antibodies of the present invention bound to one of the antigens, the binding to the second antigen was not affected. The recombinant bispecific antibodies such as AB03 and AB04 can efficiently bind to the both antigens, and both the PDL-1 and the CTLA-4 targets which play a key role in tumor immunity can be blocked, so as to inhibit the both signal pathways, thereby playing a pharmacodynamically synergistic role in tumor treatment.

TABLE 8

| Activity of recombinant bispecific antibodies binding to both PDL-1 and CTLA-4 | |
|---|---|
| Recombinant bispecific antibodies | EC50(pM) |
| AB03 | 16.24 |
| AB04 | 12.98 |

Example 5. Competitive ELISA Detection of the Blocking of PD-1/PDL-1 Binding by Recombinant Bispecific Antibodies In the present example, whether the recombinant bispecific antibodies can block the binding of PD1 to PDL-1 or not was detected by competitive ELISA.

Figure 6:
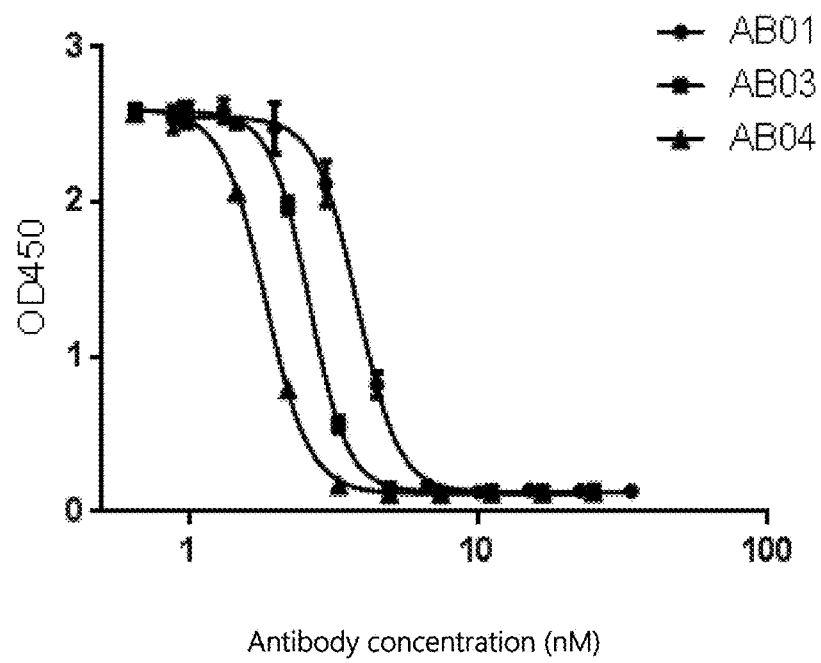
FIG. 6 shows curves of antibodies to block the binding activity of PD-1 to PDL-1.

The recombinant PD1-hFc protein (purchased from Sino Biological Inc.) was added into a 96-well enzyme labeled plate (purchased from Thermo) at 100 ng/well, and the coating was carried out at 4° C. overnight. On the next day, the solution in the wells was discarded and wells were washed one time with washing buffer (phosphate buffer solution containing 0.05% Tween-20) and the solution in the wells was discarded again. PBS solution containing 2% BSA was added at 100 μl/well for blocking the wells at 37° C. for 2 hours, and then the solution in the wells was discarded. The recombinant bispecific antibodies AB03 and AB04 and the parental antibody AB01 were diluted 1.5 folds serially at a start concentration of 10 ug/ml to get 11 concentration gradients. An equal volume of 1.6 ug/m PDL-1-mFc (obtained from Kelun-Biotech) was added and uniformly mixed, then the mixture was kept for 30 min at room temperature before adding it into the wells at 100 uL/well. The plate was incubated at 37° C. for 2 hours, then the solution in the wells was discarded and the well was washed with the washing buffer for three times. HRP conjugated goat anti-mouse IgG(H+L) (purchased from Thermo) solution was added into the plate at 100 μl/well and the plate was incubated at 37° C. for 1 hour. TMB solution was added to the wells, and the reaction was carried out at room temperature for about 5 minutes. Stop solution was added to the plate, and then the plate was put into an ELISA instrument in order to read an OD450 light absorbance value. A fitting curve was made by the means of the experimental data, as shown in FIG. 6, and EC50 was calculated.

The EC50 result was shown in Table 9, and the determined EC50 values of activities of recombinant bispecific antibody AB03 or AB04 in blocking binding of the PDL-1 to PD1 were stronger than that of the anti-PDL-1 parental antibody AB01, indicating that the recombinant bispecific antibodies of the present invention overall maintained the activities to block the binding of the PDL-1 to PD1, which were identical to or better than that of the parental antibody,

TABLE 9

| Activities to block PD1/PDL-1 binding of the recombinant antibodies | |
|---|---|
| Recombinant/ parental antibody | EC50(nM) |
| AB01 | 3.82 |
| AB03 | 2.60 |
| AB04 | 1.84 |

Example 6. CDC, ADCC Activity Detection of Recombinant Bispecific Antibodies by ELISA In the present example, the binding of the recombinant bispecific antibodies to CD16a (Val) and C1q respectively was detected by means of ELISA in order to verify the ADCC and CDC activities of the recombinant bispecific antibodies.

6.1 Detection of Binding Activity of Recombinant Bispecific Antibodies to CD16a (Val)

The recombinant CD16a (Val) protein (purchased from Sino Biological Inc.) was added into a 96-well enzyme labeled plate (purchased from Thermo) at 100 ng/well, and coating was carried out at 4° C. overnight. On the next day, the solution in the wells was discarded, the wells were washed with a washing buffer solution (a phosphate buffer solution containing 0.05% Tween-20) for one time and the solution in the wells was discarded. PBS solution containing 2% BSA was added at 100 μl/well for blocking the well at 25° C. for 2 hours, and then solution in the wells was discarded. The recombinant bispecific antibodies AB03, AB04, the parental antibody AB01 and a positive control antibody human IgG1 (obtained from Kelun-Biotech) at 50 ug/ml were crosslinked respectively with Goat F(ab)₂ anti- Human Kappa (purchased from BIORAD) at 37° C. for 1 hour, then 3-fold dilution was performed serially to get 11 concentration gradients, and the mixture was added to the well at 100 μl/well. The plate was incubated at 25° C. for 2 hours, then the solution in the wells was discarded and the well was washed with the washing buffer for three times. HRP-conjugated F(ab)$_2$ affinity purified F(ab')$_2$ fragmented goat anti-Human IgG second antibody (purchased from Jackson) at 1:10000 was added into the plate at 100 d/well and the plate was incubated at 25° C. for 1 hour. Then solution in the well was discarded and the well was washed with the washing buffer for five times. TMB solution was added to the well at a concentration of 100 μl/well, and the reaction was carried out at room temperature for about 30 minutes. Stop solution at 100 μl/well was added to the plate, and then the plate was put into an ELISA instrument to read OD450 absorbance values. A fitting curve was made by the means of the experimental data, as shown in FIG. 7.

Figure 7:
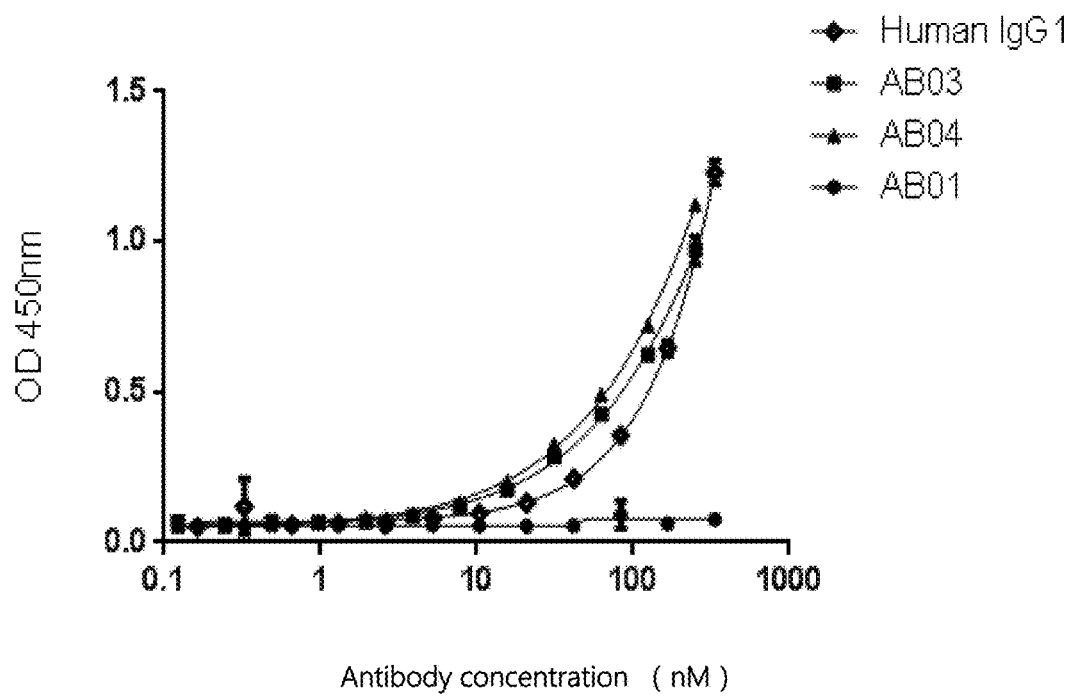
FIG. 7 shows binding activity curves of antibodies to CD16a (Val).

The result was shown in FIG. 7, and the detected recombinant bispecific antibodies AB03 and AB04 had binding activities for CD16a (Val.) protein, which was equivalent to that of human IgG1. In contrast, AB01 almost did not bind to CD16a (Val). This indicated that the recombinant bispecific antibodies of the present application had an ADCC activity.

6.2 Detection of Recombinant Bispecific Antibodies Binding Activity to C1q

The recombinant bispecific antibodies AB03, AB04 as well as the parental antibody AB01 and a positive control antibody human IgG1 (obtained from Kelun-Biotech) were diluted 3 folds serially at a start concentration of 500 ug/ml, to get 11 concentration gradients and were added to the wells of a 96-well ELISA plate at 100 μl/well. The coating was carried out at 4'C overnight. On the next day, solution in the wells was discarded, wells were washed one time with washing buffer and solution in the wells was discarded again. PBS solution containing 2% BSA was added at 100 μl/well for blocking the wells at 37° C. for 2 hours, and then solution in the wells was discarded. C1q (purchased from PROSPEC Corporation) diluted with PBS solution containing 2% BSA to a concentration of 3 ug/ml was added to the well at 100 μl/well. The plate was incubated at 37° C. for 2 hours, then the solution in the wells was discarded and wells were washed with washing buffer for 3 times, 1:200 diluted HRP anti-C1q antibody (purchased from Abcam Corporation) was added into the plate at 100 μl/well added, the plate was incubated at 37° C. for 1 hour, then solution in the wells was discarded and wells were washed with the washing buffer for 5 times. TMB solution was added to the well, and the reaction was carried out at room temperature for about 5 minutes. Stopping solution was added to the plate, and then the plate was put into an ELISA plate reader to read OD450 absorbance values. A fitting curve was made by the means of the experimental data, as shown in FIG. 8.

Figure 8:
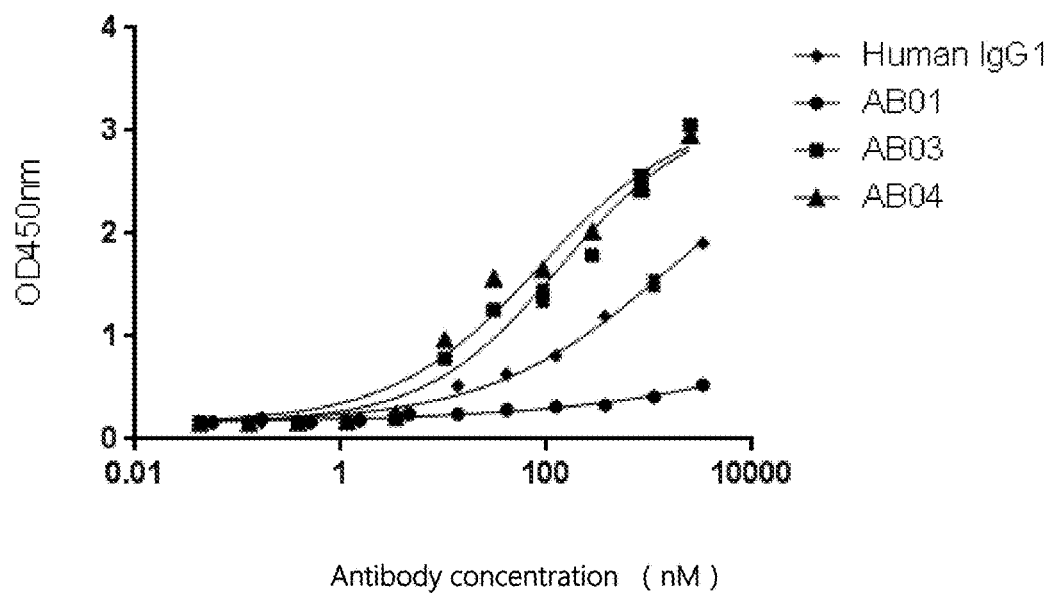
FIG. 8 shows binding activity curves of antibodies to C1q.

The result was shown in FIG. 8. The detected recombinant bispecific antibodies AB03 and AB04 had stronger binding activities to C1q protein than that of human IgG1, which indicated that these recombinant bispecific antibodies had a stronger CDC activity.

Example 7. Measurement of Thermal Denaturation Temperature Tm 7.1 Tm Values of Recombinant Bispecific Antibodies were Measured by DSF (Differential Scanning Fluorometric Method)

The recombinant bispecific antibodies and the parental antibody AB01 were diluted to 1 mg/mL with PBS solution. SYPRO® orange protein gel stain solution (Orange Protein Gel Stain, Cat #S6651) was diluted in 40 folds with distilled water, 12.5 uL diluted samples, 4.2 uL diluted SYPRO® orange protein gel staining solution, and 8.3p distilled water were sequentially added to a 0.2 ml centrifuge tube. The mixture was then put into a fluorescent quantitative PCR instrument (commercially available from Thermo Co., model 7500) and the reaction parameters were set as follows: 25° C. for 3 minutes, and increasing to 95° C. at a rate of 1%, and 95° C. for 2 minutes.

7.2 Measurement of Tm Values of the Recombinant Bispecific Antibodies by DSC (Differential Scanning Calorimetry Method)

The recombinant bispecific antibodies were diluted to 1 mg/mL with PBS solution and put into a high-throughput protein stabilization analyze (UNCHAINED LABS, Inc., model Uncle) at 9 μl/well. The reaction parameters were set as follows: 25° C. to 95° C. at a rate of 0.3° C./min.

The results of DSF and DSC were shown in Table 10. The thermal stability of the recombinant bispecific antibodies AB03 and AB04 were good. Among them, the thermal stability of AB03 was better than that of AB04, and the Tm value of AB03 was closer to those of the parental antibodies AB01 and AB02. Overall, the recombinant bispecific antibodies of the present invention had a good thermal stability.

TABLE 10

Thermal denaturation temperature of recombinant bispecific antibodies

| Recombinant/ parental antibody | AB01 | AB02 | AB03 | AB04 |
| --- | --- | --- | --- | --- |
| DSF TN(° C.) | 77.6 | 75.2 | 71.8 | 68.7 |
| DSC Tm1(° C.) | 72.0 | Not measured | 74.6 | 71.0 |
| DSC Tm2(° C.) | 81.3 | Not measured | 82.1 | 79.8 |

Example 8. Blocking PD1/PDL-1 Cell Activity by Recombinant Bispecific Antibodies A reporter assay method was used to detect the biological activity of the PD-1/PDL-1 antibody. The CHO-PDL-1-CD3L cell line, stably expressing PDL-1 and anti-CD3-scFv was used as target cells. The Jurkat-PD-1-NFAT cell line stably expressing PD-1 and luciferase was used as effector cells. The luciferase gene was regulated by the NFAT element (transcription factor) (IL-2 promoter). The binding of PD-1 to PDL-1 could block the transduction of CD3 downstream signals, thereby inhibiting the expression of luciferase. When the PD-1 antibody or PDL-1 antibody was added, this blocking effect was reversed and luciferase could be expressed so that a fluorescent signal could be detected.

Figure 9:
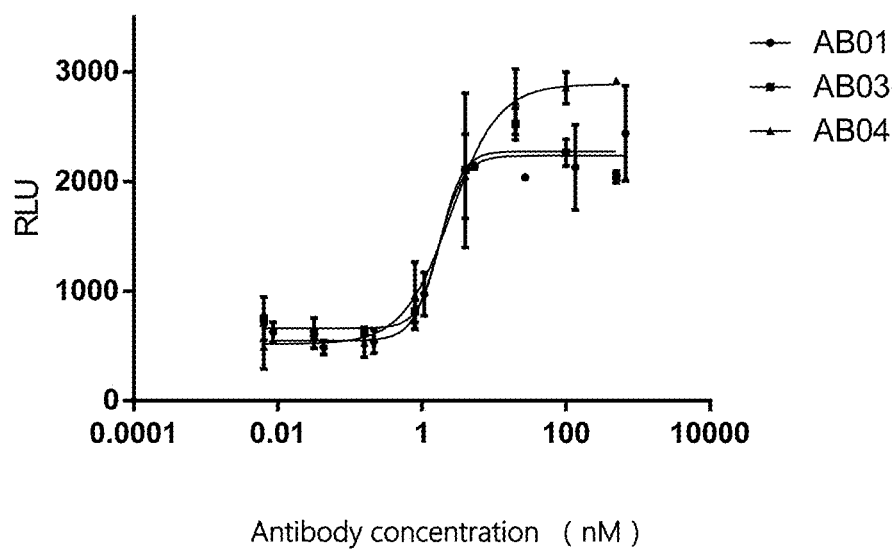
FIG. 9 shows blocking curve of antibodies PD1/PDL-1 cell binding activity.

Specific experimental procedure: The Jurkat-PD1NFAT cells and CHO-S-OKT3-PDL-1 cells (purchased from Promega) were centrifuged at 200 g for 5 min and resuspended with the assay buffer RPMI1640-1% FBS. CHO-S-OKT3-PDL-1 cells were plated at 5×10$^5$/40 μl/well. 2.5×10$^6$/40 μl/well of Jurkat-PD1-NFAT cells were added to the wells pre-plated with CHO-S-OKT3-PDL-1 cells, and 40 μL of recombinant bispecific antibodies AB003, AB04 and antibody AB01 obtained in a 5-fold dilution from a start concentration of 100 μg/mL were added. After co-incubation for 6 hours, the co-cultures were taken out, left at room temperature for 20 min, and 60 μL detection reagent Bright-Glo Luciferase (purchased from Promega) was added, then shaken at room temperature for 5 min, and detected by a microplate reader (BMG. PHEARstar FS). A fitting curve was made from the experimental data by GraphPad prism 5 and the EC50 was calculated, as shown in FIG. 9.

The results were shown in Table 11, and EC50 values of the activities of the detected recombinant bispecific antibodies AB03 and AB04 in blocking the cellular activity of PDL-1 binding to PD1 were equivalent to that of the anti-PDL-1 parental antibody AB01, indicating that the recombinant bispecificantibodies of the present invention overall maintained the cellular activity to block PDL-1 binding to PD1 as excellent as that of the parental antibody.

TABLE 11

Activity of the recombinant antibodies to block PDL-1/PD1

| Recombinant/ parental antibody | EC50(nM) |
|---|---|
| AB01 | 1.68 |
| AB03 | 1.82 |
| AB04 | 1.53 |

Example 9. Recombinant Bispecific Antibodies Enhanced IL-2 Secretion Activity by T Cells in SEB-Stimulated PBMCs MHC II on APC cells can be crosslinked with TCR of T cells by super antigen (SEB) to activate T cells and promote IL-2 cytokine expression. Binding of PD1 on T cells to PDL-1 on APC cells, and binding of CTLA-4 on T cells to CD80/CD86 on APC cells could inhibit T cell activation and decrease IL-2 cytokine expression. The recombinant bispecific antibody of the present invention could block the binding of PD1/PDL-1 and CTLA-4/CD80 (CD86), and further promote secretion of IL-2 by T cell in SEB-stimulated PBMCs.

Specific experimental procedure: PBMC cells were resuscitated and resuspended with 5 mL RPM11640+10% FBS (fetal calf serum) with 85% cell viability and $8 \times 10^5$ cells/ml viable cell density. The cells were cultured at 37° C. in a $CO_2$ incubator for more than 2 hours. 120 μL cell suspension was added to the wells at $10^5$ cells/well. 2.5 ng/mL SEB (from Chinese Academy of Sciences) antibody diluents was prepared with RPM11640+10% FBS and recombinant bispecific antibodies AB03, AB04 and control antibody AB01, AB02 were diluted, respectively, 80 μL antibody diluents were added to corresponding wells, mixed and placed in a $CO_2$ incubator at 37° C. for 3 days. The supernatant were taken for IL-2 expression detection by an IL-2 test kit (purchased from CisBio).

Figure 10:
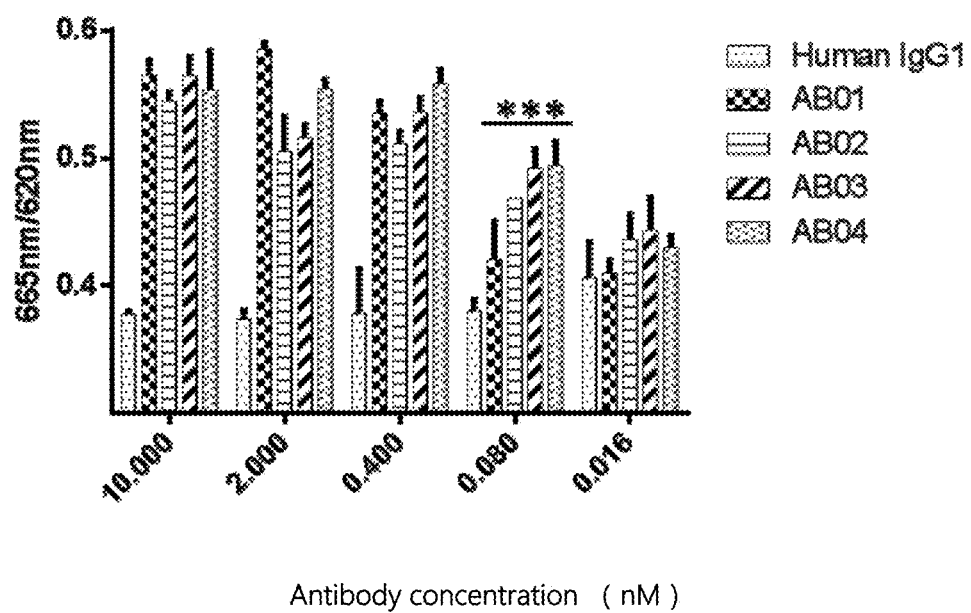
FIG. 10 shows the activity charts of antibodies enhancing IL-2 secretion by T cells in the presence of SEB-stimulated PBMCs.

The results were shown in FIG. 10, and overall, the detected recombinant bispecific antibodies AB03 and AB04 parental antibody significantly increased IL-2 secretion in SEB-stimulated PBMCs compared with the parental antibodies AB01 and AB02. Moreover, the recombinant bispecific antibodies and the parental antibody exerted the maximum response values at high concentrations. Under the condition of a low concentration of antibodies, the function of recombinant bispecific antibodies AB03 and AB04 was enhanced to some extent compared with the parent antibodies AB01 and AB02 (marked with asterisk).

Example 10. In Vivo Efficacy of PDL-1 Antibody AB01 on Colon Cancer

1. Experimental Drugs

AB01, Tecentriq®, and human IgG were provided by Sichuan Kelun Pharmaceutical Research Institute Co., Ltd.; Tecentriq® was purchased from Roche Company, and human IgG was purchased from Chengdu Rongsheng Pharmaceutical Co., Ltd.

Preparation method: All three drugs were diluted to the required concentration with 0.1% BSA physiological saline.

2. Experimental Cells and Animals

MC-38/H-11 cells were monoclonal cells obtained by knocking out mouse endogenous PDL-1 of mouse colon cancer MC-38 (purchased from Cobioer, Cat. No. CBP60825) cells, transfecting with human PDL-1 and expressing human PDL-1. Therefore MC-38/H-11 cells only express high level of human PDL-1 protein.

C57BL/6 mice, 7-8 weeks, ♀, were purchased from Shanghai Slack Laboratory Animals Co., Ltd.

3. Experimental Steps

Each mouse was subcutaneously inoculated with $1 \times 10^5$ MC-38/H-11 cells. The next day alter inoculation (D0), the mouse was randomly grouped and drugs were injected by intraperitoneal injection (IP), once every other day (Q2D). A solvent group receiving injection of human IgG38 (15 mg/kg), AB01 (1.5, 5, 15 mg/kg), Tecentriq® (15 mg/kg), injection volume of each mouse was 0.1 mL/10 g body weight. Each group had 10 mice.

4. Experimental Indicators

The experimental indicators were used to investigate the effect of drugs on tumor growth. The specific indicators were T/C % or tumor inhibition rate TGI (V %).

The tumor diameters were measured twice a week with a vernier caliper. The tumor volume (V) was calculated as: $V = \frac{1}{2} \times a \times b^2$, where a and b represented length and width, respectively.

T/C %=T/C×100, C and T were the tumor volume or tumor weight of the solvent group and the treatment group, respectively.

Tumor inhibition rate (TGI) (%)=(C−T)/C×100, C and T were the tumor volume or tumor weight of the solvent group and the treatment group, respectively.

5. Experimental Results

The results were shown in Table 12 below.

TABLE 12

Effect of AB01 (1.5, 5, 15 mg/kg) and Tecentriq ® on a subcutaneous transplant tumor of mouse colon cancer MC-38/H-11 mice

| Groups/ administering dose | Mean tumor volume (mm³)D 27 | T/C % D 27 | Tumor inhibition rate(TGI)% | Median tumor volume (mm³) D 27 | Tumor inhibition rate(TGI)(%) | Median tumor weight (g) D 27 | Tumor inhibition rate(TGI)% | Tumor formation rate % |
|---|---|---|---|---|---|---|---|---|
| Human IgG (15 mg/kg) | 2486.0 | — | — | 2126.7 | — | 25.0 | — | 100.0 |
| AB01 (1.5 mg/kg) | 898.5 | 36.1 | 63.9 | 0.0 | 100.0 | 0.0 | 100.0 | 40.0 |

TABLE 12-continued

Effect of AB01 (1.5, 5, 15 mg/kg) and Tecentriq ® on a subcutaneous transplant tumor of mouse colon cancer MC-38/H-11 mice

| Groups/<br>administering dose | Mean<br>tumor<br>volume<br>(mm³) D 27 | T/C %<br>D 27 | Tumor<br>inhibition<br>rate(TGI)% | Median<br>tumor<br>volume<br>(mm³) D 27 | Tumor<br>inhibition<br>rate(TGI)(%) | Median<br>tumor<br>weight<br>(g) D 27 | Tumor<br>inhibition<br>rate(TGI)% | Tumor<br>formation<br>rate % |
|---|---|---|---|---|---|---|---|---|
| AB01<br>(5 mg/kg) | 600.6 | 24.2 | 75.8 | 0.0 | 100.0 | 0.0 | 100.0 | 40.0 |
| AB01<br>(15 mg/kg) | 780.6 | 31.4 | 68.6 | 0.0 | 100.0 | 0.0 | 100.0 | 40.0 |
| Tecentriq<br>(15 mg/kg) | 867.2 | 34.9 | 65.1 | 132.0 | 93.8 | 0.2 | 93.7 | 50.0 |

Note:
Randomly grouped, the first administration time was D 0; D 27 was the 27th day after administration.

The tumor inhibition rates of AB01 (1.5, 5, 15 mg/kg) on a subcutaneous xenograft tumor of MC-381H-11 mice were 63.9%, 75.8% and 68.6%, respectively (calculated based on the mean tumor volume). It was more reasonable to calculate tumor inhibition rate based on the median tumor volume since the individual differences in every group were large, then, the tumor inhibition rates were adjusted to 100%, 100%, and 100%. The tumor inhibition rate of the reference drug Tecentriq® (15 mg/kg) for MC-38/H-11 was 93.8% (calculated according to the median tumor volume). The tumor inhibition rates of AB01 (15, 5, 15 mg/kg) for MC-38/H-11 were 100%, 100%, 100%, and the tumor inhibition rates of Tecentriq® was 93.7% calculated according to the median tumor weight. The tumor inhibition rates calculated according to the median tumor volumes were very consistent with those calculated from the median tumor weight, indicating tumor volume measurement methods were liable. AB01 (1.5, 5, 15 mg/kg) could not only inhibit tumor growth, but also inhibit tumor formation. At the end of the experiment (D27), the tumor formation rates of the dose groups of AB01 (1.5, 5, 15 mg/kg) were 40%, 40% and 40% respectively, while the tumor formation rate of the Tecentriq® group was 50%. The tumor-bearing mice well tolerated the above drugs, and no obvious weight loss and other symptoms occurred. Compared to Tecentriq®, AB01 (1.5, 5, 15 mg/kg) had a stronger anti-tumor effect on subcutaneous xenograft tumor of mouse colon cancer MC-38H-11.

Example 11. In Vivo Efficacy of PDL-1 Antibody AB01 on Lung Cancer

Modeling method: Non-small cell lung cancer cells HCC827 (purchased from ATCC, Cat #: CRL-2868) were subcutaneously inoculated into NOG mice to construct a lung cancer tumor-bearing mouse model. When the tumors reached up to about 100 mm³, the activated human PBMCs were intravenously injected to the mice in order to simulate the human immune system before administration. Then the drugs were administrated.

Dosing regimen: The drugs were intravenously injected at a dose of 10 mg/kg once every two days for a total of four doses. Tumor volume was measured twice a week after administration. Mice were divided into three groups, which were control IgG, AB01, Tecentriq® groups, 6 mice in each group.

Figure 11:
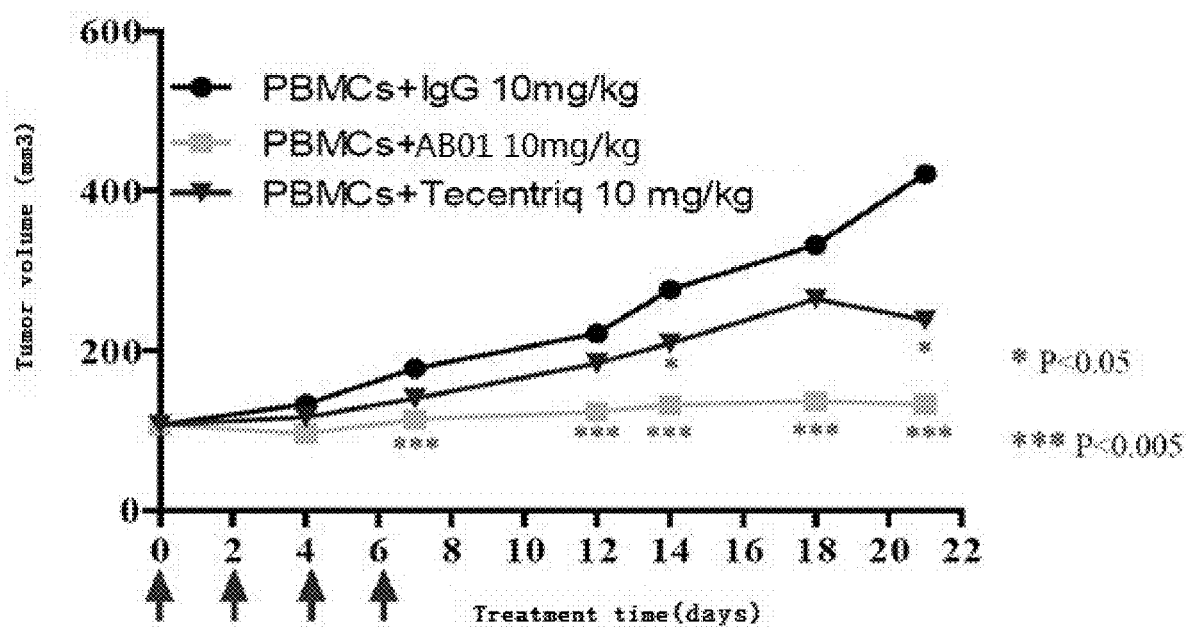
FIG. 11 shows the efficacy of AB01 in a non-small cell lung cancer model.

The tumor growth curves were shown in FIG. 11.

The results showed that from Day 4, the tumor volume of the AB01 group was significantly smaller than those of the Tecentriq® group and the IgG control group. The tumor growth of AB01 group was almost completely inhibited, while the tumors of the Tecentriq® group and the IgG control group were continuously grew confirming that the AB01 antibody had a stronger anti-tumor effect than Tecentriq® in vivo.

Figure 12:
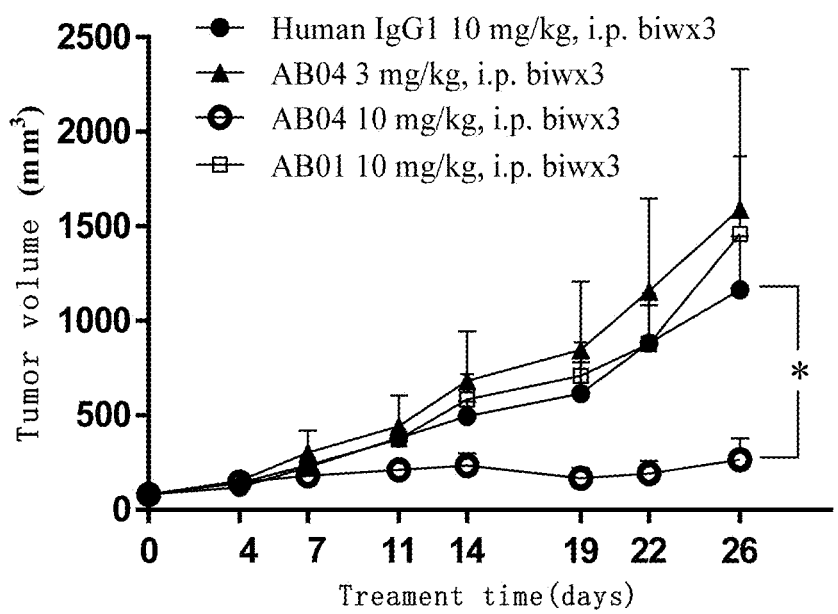
FIG. 12 shows the efficacy of antibodies in a mouse model of colon cancer.

Example 12. Test of Recombinant Bispecific Antibodies in a Transgenic Colon Cancer Mouse Model MC38-1F3 cells were cultured in RPMI1640 medium containing 10/o fetal bovine serum at 37° C., 5% $CO_2$. Then MC38-1F3 cells in exponential growth phase were collected, resuspended in PBS to a proper concentration, and inoculated into female C57BL/6J-huCTLA-4 (purchased from Gempharmatech) mice subcutaneously to establish a colon cancer model. When the average tumor volume was about 82 mm³, according to tumor sizes, mice were randomly grouped in to four groups which were intravenous injection human immunoglobulin group (negative control group), AB01 control group, AB04 low-dose group and AB04 high-dose group. The drugs were intraperitoneally injected twice a week for a total of 3 weeks administration. The tumor volume and body weight of the mice were observed and measured periodically after administration. The results were shown in Table 13 and FIG. 12.

According to the results, the anti-tumor effect of AB04 antibody low-dose group (3 mg/kg) on MC38-1F3 colon cancer transplant tumor model was better than that of AB01, and its high-dose group (10 mg/kg) had a significantly better anti-tumor effect than the low-dose group and the anti-tumor effect was significant. All mice of the treatment groups did not have animal death or significant animal weight loss, nor manifested significant drug toxicity during the observation period. The mice well tolerated AB04 antibody during the treatment period.

TABLE 13

Effect of recombinant bispecific antibodies on colon cancer in mice

| | | P26 | | | |
|---|---|---|---|---|---|
| Group | Regimen | Tumor volume<br>(mm³)<br>(x ± SEM) | TGI<br>(%) | T/C<br>(%) | P value<br>(vs.goup 1) |
| 1 | Human IgG<br>10 mg/kg | 1164.44 ± 284.32 | — | — | — |
| 2 | AB04<br>3 mg/kg | 1589.72 ± 741.91 | 39.21 | 135.34 | 0.61 |
| 3 | AB04<br>10 mg/kg | 265.39 ± 113.35 | 83.02 | 22.76 | 0.019 |
| 4 | AB01<br>10 mg/kg | 1460.04 ± 410.43 | 27.26 | 124.81 | 0.57 |

Figure 13:
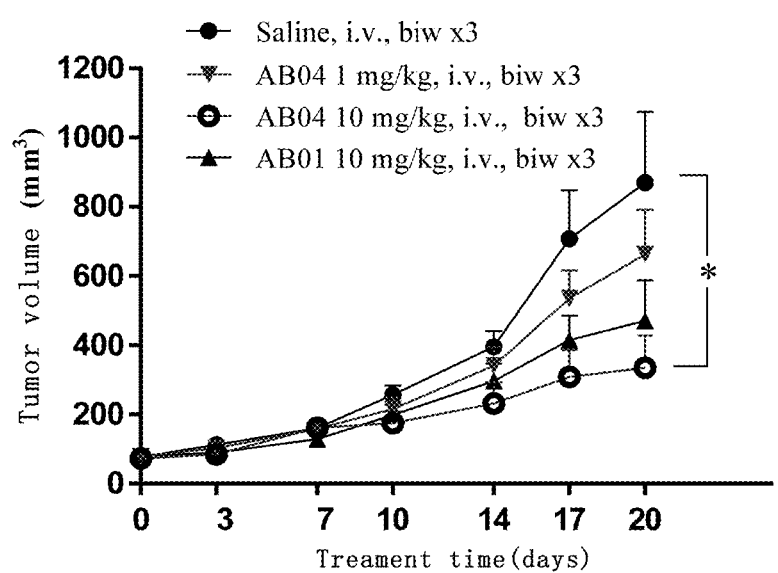
FIG. 13 shows the efficacy of antibodies in a mouse model of non-small cell lung cancer.

Example 13. Test of Recombinant Bispecific Antibodies in a Transgenic Non-Small Cell Lung Cancer Mouse Model The human non-small cell lung cancer HCC827 cells was cultured in RPM11640 medium containing 10% fetal bovine serum at 37° C., 5% $CO_2$. HCC827 cells in the exponential growth phase were collected, resuspended in PBS to a suitable concentration, and inoculated into female NSG immunodeficient mice to subcutaneously establish a transplant tumor model (hPBMC-NSG (purchased from Biocytogen)-HCC827 human immuno-reconstruction model). When the average tumor volume reached about 77 $mm^3$, according to tumor size, mice were randomly grouped to four groups which were saline group (negative control group), AB01 control group, AB04 low-dose group and AB04 high-dose group, Human peripheral blood mononuclear cells PBMCs were cultured in RPMI 1640 medium containing 10% fetal bovine serum, CD28/CD3 antibodies and DNase at 37° C. 5% $CO_2$. After 3 days of stimulation with CD3 and CD28 antibodies, activated PBMCs were harvested, resuspended in PBS to a proper concentration, and injected into tail veins of grouped female NSG mice to reconstruct their immune systems. The mice were injected with drugs vital veins twice a week for a total of 3 weeks administration after being grouped as mentioned above. The tumor volume and body weight of the mice were observed and measured periodically after administration. The results were shown in Table 14 and FIG. 13.

TABLE 14

Effect of recombinant bispecific antibodies on transgenic non-small cell lung cancer mice

| | | P20 | | | |
|---|---|---|---|---|---|
| Group | Regimen | Tumor volume $(mm^3)$ (x ± SEM) | TGI (%) | T/C (%) | P value (vs.group 1) |
| 1 | Saline | 885.99 ± 204.92 | — | — | — |
| 2 | AB04 1 mg/kg | 662.40 ± 129.36 | 27.95 | 72.17 | 0.41 |
| 3 | AB04 10 mg/kg | 334.35 ± 93.35 | 67.72 | 39.40 | 0.039 |
| 4 | AB01 10 mg/kg | 470.21 ± 116.86 | 51.74 | 50.91 | 0.12 |

According to the results, the low dose group of AB04 antibody (1 mg/kg) had some inhibitory effect on the tumor growth of NSG immune reconstruction mice which were subcutaneously transplanted with human non-small cell lung cancer HCC827 cells, and the high-dose group (10 mg/kg) had a significant anti-tumor efficacy. AU the treatment groups did not have animal death or significant weight loss, nor exhibited significant drug toxicity during the observation period, the mice well tolerated the antibodies during the treatment period.

Example 14. Toxicological Study of Recombinant Bispecific Antibodies

To study the toxicology of recombinant bispecific antibodies in cynomolgus monkeys, AB04 was intravenously injected into cynomolgus monkeys (one male and one female) as single dose administration, and a saline group served as a control group. The recovery period was 14 days. The experimental results showed that cynomolgus monkeys well tolerated a single dose of intravenous injection of 500 mg/kg AB04, and the MTD was 500 mg/kg. Repeated administration was given at a dose of 100 mg/kg once a week for 5 consecutive doses. There was no significant target toxicity to the target organs and irritation to the site of administration, and NOAEL (no observed adverse effect level) was 100 mg/kg. According to the existing research datas published by FDA, the anti-CTLA-4 antibody Ipilimumab (trade name: Yervoy) when repeatedly administered, the NOAEL was 10 mg/kg (at this dose, the spleen weight reduced after administration, and mild toxicity such as a multiple organ lymphocyte infiltration was observed). The MTD of Ipilimumab was 30 mg/kg. AB04 reduced the toxicity of CTLA-4 antibody and improved the safety of the drug to some extent.

Although specific embodiments of the invention have been described in detail, those skilled in the art will understand that, various modifications and changes can be made in the details, and such changes are within the scope of the invention. The scope of the invention is embodied by the appended claims and any equivalents thereof.

The invention claimed is:

1. A bispecific antibody comprising:
1) a first antibody that specifically binds to a first antigen, the first antibody comprising heavy chains (HCs) and light chains (LCs); and
2) a scFv that specifically binds to a second antigen; wherein:
the scFv is linked to the N-terminus or C-terminus of the heavy chain or light chain of the first antibody;
the first antigen is CTLA-4, and the second antigen is PDL-1; or the first antigen is PDL-1, and the second antigen is CTLA-4;
the bispecific antibody comprises one said first antibody and two said scFvs;
and said first antibody comprises two HCs and two LCs, wherein the VH region of one of the HCs and the VL region of one of the LCs of said first antibody form an antigen binding site, and the VH region of the other HC and the VL region of the other LC of said first antibody form an antigen binding site;
one of the scFvs is linked to the N-terminus of the heavy chain or light chain of the first antibody, and the other scFv is linked to the C-terminus of the heavy chain or light chain of the first antibody; or
each of said scFvs is linked to the N-terminus of two heavy chains or two light chains of said first antibody, respectively; or each of said scFvs is linked to the C-terminus of two heavy chains or two light chains of said first antibody, respectively;
and wherein:
(a) said first antibody specifically binds to CTLA-4 and comprises a HCDR1 set forth in SEQ ID NO: 13, a HCDR2 set forth in SEQ ID NO: 14 and a HCDR3 set forth in SEQ ID NO: 15 in the VH region of one of the HCs, and a LCDR1 set forth in SEQ ID NO: 16, a LCDR2 set forth in SEQ ID NO: 17 and a LCDR3 set forth in SEQ ID NO: 18 in the VL region of one of the LCs; and said scFv specifically binds to PDL-1 and comprises a HCDR1 set forth in SEQ ID NO: 1, a HCDR2 set forth in SEQ ID NO: 2, a HCDR3 set forth in SEQ ID NO: 3, a LCDR1 set forth in SEQ ID NO: 4, a LCDR2 set forth in SEQ ID NO: 5, and a LCDR3 set forth in SEQ ID NO: 6; or
(b) said first antibody specifically binds to PDL-1 and comprises a HCDR1 set forth in SEQ ID NO: 1, a HCDR2 set forth in SEQ ID NO: 2 and a HCDR3 set forth in SEQ ID NO: 3 in the VH region of one of the HCs, and a LCDR1 set forth in SEQ ID NO: 4, a LCDR2 set forth in SEQ ID NO: 5 and a LCDR3 set forth in SEQ ID NO: 6 in the VL region of one of the LCs, and said scFv specifically binds to CTLA-4 and comprises a HCDR1 set forth in SEQ ID NO: 13, a HCDR2 set forth in SEQ ID NO: 14, a HCDR3 set forth in SEQ ID NO: 15, a LCDR1 set forth in SEQ ID NO: 16, a LCDR2 set forth in SEQ ID NO: 17, and a LCDR3 set forth in SEQ ID NO: 18.

2. The bispecific antibody of claim 1 comprising:
1) a first antibody that specifically binds to the first antigen, the first antibody comprising heavy chains (HCs) and light chains (LCs); and
2) a scFv that specifically binds to the second antigen;
wherein the bispecific antibody comprises one said first antibody and two said scFvs; and said first antibody comprises two HCs and two LCs, wherein the VH region of one of HCs and the VL region of one LC of said first antibody form an antigen binding site, and the VH region of the other HC and the VL region of the other LC of said first antibody form an antigen binding site;
wherein each of said scFvs is linked to the N-terminus of two heavy chains of said first antibody, respectively; or each of said scFvs is linked to the C-terminus of two heavy chains of said first antibody, respectively;
wherein the first antigen is PDL-1 and the second antigen is CTLA-4;
wherein each of the scFvs is linked to the N-terminus or C-terminus of each heavy chain of the first antibody via a linker S1; and
wherein the VH and VL of said scFv are linked by a linker S2.

3. The bispecific antibody of claim 2, the structure of the scFv is NH2-VL-S2-VH-COOH.

4. The bispecific antibody of claim 1, wherein the heavy chain of the first antibody comprises a heavy chain variable region (VH) and a heavy chain constant region (CH), and the light chain comprises a light chain variable region (VL) and a light chain constant region (CL); or
the first antibody is a full length antibody.

5. The bispecific antibody of claim 1, wherein the first antibody is an IgG isotype; and/or, the light chain of the first antibody is a Kappa isotype.

6. The bispecific antibody of claim 5, wherein the first antibody is a IgG1, IgG2, IgG3 or IgG4 isotype; and/or the light chain of the first antibody is a Kappa isotype.

7. The bispecific antibody of claim 5, wherein the first antibody is a human IgG1, IgG2, IgG3 or IgG4 isotype; and/or the light chain of the first antibody is a human Kappa isotype.

8. The bispecific antibody of claim 1, wherein the CDRs of two HCs of the first antibody are the same; and/or the CDRs of two LCs of the first antibody are the same;

wherein the two HCs of the first antibody comprise the same VH; and/or the two LCs of the first antibody comprise the same VL;

wherein the two HCs of the first antibody have the same amino acid sequence; and/or the two LCs of the first antibody have the same amino acid sequence; and wherein the two scFvs have the same or different amino acid sequences.

9. The bispecific antibody of claim 1, wherein the bispecific antibody comprises two first polypeptide chains and two second polypeptide chains, wherein for each of the polypeptide chains:
  a) each of said first polypeptide chains independently comprises a heavy chain (HC) of said first antibody and said scFv; and
  b) each of said second polypeptide chains independently comprises a light chain (LC) of said first antibody;
  wherein the scFv is linked to the N-terminus or C-terminus of the HC of the first antibody via a linker S1;
  or,
  i) each of said first polypeptide chains independently comprises a light chain (LC) of said first antibody and said scFv; and
  ii) each of said second polypeptide chains independently comprises a heavy chain (HC) of said first antibody;
  wherein said scFv is linked to the N-terminus or C-terminus of the LC of the first antibody via a linker S1;
  wherein said scFv has the structure: NH$_2$-VH-S2-VL-COOH or NH$_2$-VL-S2-VH-COOH, wherein said S2 is a linker; and
  wherein said bispecific antibody comprises two identical first polypeptide chains and two identical second polypeptide chains.

10. An isolated nucleic acid molecule, which comprises a nucleotide sequence encoding the bispecific antibody of claim 9;
  wherein the isolated nucleic acid molecule comprises a nucleotide sequence encoding the first polypeptide chain of the bispecific antibody of claim 9; and
  wherein the isolated nucleic acid molecule comprises a nucleotide sequence encoding the second polypeptide chain of the bispecific antibody of claim 9.

11. The bispecific antibody of claim 1, wherein said bispecific antibody has the binding activity to the first antigen equal to or weaker than that of the parental antibody of said first antibody; and wherein:
  said bispecific antibody has the binding activity to the second antigen equal to or weaker than that of the parental antibody of said scFv; or
  said bispecific antibody has the binding activity to the first antigen equal to or weaker than that of the parental antibody of said first antibody and the binding activity to the second antigen equal to or weaker than that of the parental antibody of said scFv; or
  said bispecific antibody has the binding activity to the first antigen equal to that of the parental antibody of said first antibody and the binding activity to the second antigen weaker than that of the parental antibody of said scFv; or
  said bispecific antibody has the binding activity equal to that of the parental antibody binding to PDL-1; or
  said bispecific antibody has the binding activity weaker than that of the parental antibody binding to CTLA-4; or
  said bispecific antibody has the binding activity equal to that of the parental antibody binding to PDL-1 parental antibody, and has the binding activity weaker than that of the parental antibody binding to CTLA-4.

12. The bispecific antibody of claim 2, wherein the linker S1 and/or S2 is a peptide linker; or
  said linker S1 and/or S2 has an amino acid sequence as shown in $(G_4S)_x$, x is selected from integers of from 1 to 6 independently; or
  the S1 and/or S2 has an amino acid sequence selected from the group consisting of: SEQ ID NO: 25, SEQ ID NO: 26 and SEQ ID NO: 27; or
  the linker S2 has an amino acid sequence set forth in SEQ ID NO: 25; and when the scFv is linked to the N-terminus of the heavy or light chain of the first antibody, the linker S1 has an amino acid sequence set forth in SEQ ID NO: 26; and when the scFv is linked to the C-terminus of the heavy chain or light chain of the first antibody, the linker S1 has an amino acid sequence set forth in SEQ ID NO: 27.

13. The bispecific antibody of claim 12, wherein the linker S1 and/or S2 is a peptide linker having an amino acid sequence as shown in $(G_mS_n)_x$, wherein each of m and n is independently selected from integers from 1 to 8, and x is independently selected from integers from 1 to 20.

14. The bispecific antibody of claim 1, wherein a disulfide bond exists between the VH and VL of the scFv;
  wherein the amino acid of the position 44 of the VH and the amino acid of the position 100 of the VL of the scFv are cysteines, respectively, wherein the amino acid position referred to is according to the Kabat numbering system; and wherein the VH and the VL of the scFv are linked through a disulfide bond formed between two cysteine residues at the position 44 of the VH and the position 100 of the VL.

15. The bispecific antibody of claim 1, wherein the first antibody specifically binds to CTLA-4, and the scFv specifically binds to PDL-1.

16. The bispecific antibody of claim 1, wherein the scFv comprises:
  (1) a VH set forth in SEQ ID NO: 7 and a VL set forth in SEQ ID NO: 9; or
  (2) a VH set forth in SEQ ID NO: 8 and a VL set forth in SEQ ID NO: 10.

17. The bispecific antibody of claim 1, wherein the first antibody comprises a VH set forth in SEQ ID NO: 19 and a VL set forth in SEQ ID NO: 21; and the scFv comprises:
  (1) a VH set forth in SEQ ID NO: 7 and a VL set forth in SEQ ID NO: 9; or
  (2) a VH set forth in SEQ ID NO: 8 and a VL set forth in SEQ ID NO: 10.

18. The bispecific antibody of claim 1, wherein the first antibody specifically binds to PDL-1, and the scFv specifically binds to CTLA-4.

19. The bispecific antibody of claim 1, wherein the first antibody comprises a VH set forth in SEQ ID NO: 7 and a VL set forth in SEQ ID NO: 9.

20. The bispecific antibody of claim 1, wherein the first antibody comprises a VH set forth in SEQ ID NO: 7 and a VL set forth in SEQ ID NO: 9; and the scFv comprises:
  (1) a VH set forth in SEQ ID NO: 19 and a VL set forth in SEQ ID NO: 21; or
  (2) a VH set forth in SEQ ID NO: 20 and a VL set forth in SEQ ID NO: 22.

21. The bispecific antibody of claim 1, wherein said bispecific antibody has an antibody-dependent cell-mediated cytotoxicity (ADCC) activity and/or a complement dependent cytotoxicity (CDC) activity;

wherein a CH of said first antibody comprises a mutation, and the bispecific antibody comprising said mutation has an enhanced antibody-dependent cell-mediated cytotoxicity (ADCC) activity; and/or wherein a CH of said first antibody comprises a mutation, and the bispecific antibody comprising said mutation has an enhanced complement dependent cytotoxicity (CDC) activity.

22. The bispecific antibody of claim 1, wherein the first antibody comprises: a CH as set forth in SEQ ID NO: 33; and/or, a CL as set forth in SEQ ID NO: 34,
optionally, the CH comprises mutations, in which the amino acid sat the positions 117, 118, and 120 in the CH as set forth in SEQ ID NO: 33 are mutated to A; or, the CH comprises a mutation, in which the amino acid at the position 97 in the CH as set forth in SEQ ID NO: 33 is mutated to R.

23. The bispecific antibody of claim 1, wherein the bispecific antibody comprises:
(1) a first polypeptide chain set forth in SEQ ID NO: 28 and a second polypeptide chain set forth in SEQ ID NO: 11; or
(2) a first polypeptide chain set forth in SEQ ID NO: 29 and a second polypeptide chain set forth in SEQ ID NO: 11.

24. The bispecific antibody of claim 1, wherein the bispecific antibody has substantially the same thermal stability as that of the parental antibody.

25. An isolated nucleic acid molecule, which comprises a nucleotide sequence encoding the bispecific antibody of claim 1.

26. A vector comprising the isolated nucleic acid molecule of claim 25.

27. A host cell comprising the vector of claim 26.

28. A method for preparing a bispecific antibody, wherein the method comprises culturing the host cells of claim 27 under a condition which permits the bispecific antibody to be expressed, and obtaining the bispecific antibody from the host cell culture.

29. A pharmaceutical composition, which comprises the bispecific antibody of claim 1, and a pharmaceutically acceptable carrier and/or excipient;
wherein the pharmaceutical composition further comprises an additional pharmaceutically active agent for treating a disease associated with CTLA-4 and/or PDL-1; and wherein the disease associated with CTLA-4 and/or PDL-1 is an autoimmune disease, a tumor or an infectious disease; wherein said tumor includes, leukemia, lymphoma, melanoma, sarcoma, or includes tumors related to adrenal gland, gallbladder, bone, bone marrow, brain, breast, bile duct, gastrointestinal tract, heart, kidney, liver, lung, muscle, ovary, pancreas, parathyroid gland, penis, prostate, skin, salivary gland, spleen, testicle, thymus, thyroid, and uterus; and wherein said infectious disease includes hepatitis B, hepatitis A, and HIV.

30. The pharmaceutical composition of claim 29, wherein the additional pharmaceutically active agent is a drug.

31. The pharmaceutical composition of claim 30, wherein the drug is an anti-inflammatory drug or an immunosuppressive agent.

32. A method for treating a disease associated with CTLA-4 and/or PDL-1 in a subject and/or a method for inhibiting the activity of CTLA-4 and/or PDL-1 in vitro or in vivo of a subject, wherein the method comprises administering to the subject in need thereof an effective amount of the bispecific antibody of claim 1, or pharmaceutical composition comprising the bispecific antibody of claim 1, and a pharmaceutically acceptable carrier and/or excipient; wherein the pharmaceutical composition further comprises an additional pharmaceutically active agent for treating a disease associated with CTLA-4 and/or PDL-1;
wherein the disease associated with CTLA-4 and/or PDL-1 is an autoimmune disease, a tumor or an infectious disease; wherein said tumor includes adenocarcinoma, leukemia, lymphoma, melanoma, sarcoma or includes tumors related to adrenal gland, gallbladder, bone, bone marrow, brain, breast, bile duct, gastrointestinal tract, heart, kidney, liver, lung, muscle, ovary, pancreas, parathyroid gland, penis, prostate, skin, salivary gland, spleen, testicle, thymus, thyroid and uterus; wherein said infectious disease includes hepatitis B, hepatitis A, and HIV; and wherein the subject is a mammal or a human.

33. The method of claim 32, wherein the additional pharmaceutically active agent is a drug.

34. The method of claim 33, wherein the drug is an anti-inflammatory drug or an immunosuppressive agent.

35. A pharmaceutical composition, which comprises the bispecific antibody of claim 23, and a pharmaceutically acceptable carrier and/or excipient; wherein the pharmaceutical composition further comprises an additional pharmaceutically active for treating a disease associated with CTLA-4 and/or PDL-1, and
wherein the disease associated with CTLA-4 and/or PDL-1 is an autoimmune disease, a tumor or an infectious disease; wherein said tumor includes adenocarcinoma, leukemia, lymphoma, melanoma, sarcoma, or, includes tumors related to adrenal gland, gallbladder, bone, bone marrow, brain, breast, bile duct, gastrointestinal tract, heart, kidney, liver, lung, muscle, ovary, pancreas, parathyroid gland, penis, prostate, skin, salivary gland, spleen, testicle, thymus, thyroid, and uterus; and wherein said infectious disease includes hepatitis B, hepatitis A, and HIV.

36. The pharmaceutical composition of claim 35, wherein the additional pharmaceutically active agent is a drug.

37. The pharmaceutical composition of claim 36, wherein the drug is an anti-inflammatory drug or an immunosuppressive agent.

38. A method for treating a disease associated with CTLA-4 and/or PDL-1 in a subject, and/or a method for inhibiting the activity of CTLA-4 and/or PDL-1 in a subject, wherein the method comprises administering to the subject in need thereof an effective amount of the bispecific antibody of claim 23, or a pharmaceutical composition comprising the bispecific antibody of claim 23, and a pharmaceutically acceptable carrier and/or excipient;
wherein the pharmaceutical composition further comprises an additional pharmaceutically active agent for treating a disease associated with CTLA-4 and/or PDL-1;
wherein the disease associated with CTLA-4 and/or PDL-1 is an autoimmune disease, a tumor or an infectious disease; wherein said tumor includes adenocarcinoma, leukemia, lymphoma, melanoma, sarcoma, or includes tumors related to adrenal gland, gallbladder, bone, bone marrow, brain, breast, bile duct, gastrointestinal tract, heart, kidney, liver, lung, muscle, ovary, pancreas, parathyroid gland, penis, prostate, skin, salivary gland, spleen, testicle, thymus, thyroid and uterus; wherein said infectious disease includes hepatitis B, hepatitis A, HIV;
and wherein the subject is a mammal, or a human.

39. The method of claim 38, wherein the additional pharmaceutically active agent is a drug.

40. The method of claim 39, wherein the drug is an anti-inflammatory drug or an immunosuppressive agent.

* * * * *

UNITED STATES PATENT AND TRADEMARK OFFICE
CERTIFICATE OF CORRECTION

PATENT NO. : 11,421,029 B2  
APPLICATION NO. : 16/624408  
DATED : August 23, 2022  
INVENTOR(S) : Xue et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 179 days.

Signed and Sealed this  
Eleventh Day of February, 2025

Coke Morgan Stewart  
*Acting Director of the United States Patent and Trademark Office*